United States Patent
Lee et al.

(10) Patent No.: US 8,372,594 B2
(45) Date of Patent: Feb. 12, 2013

(54) SECRETED PHOSPHOLIPASE A2 BIOMARKERS FOR ARTHRITIS

(75) Inventors: David M. Lee, Basel (CH); Eric Boilard, Quebec (CA); Michael H. Gelb, Seattle, WA (US); Reuben Gobezie, Cleveland Heights, OH (US)

(73) Assignees: Case Western Reserve University, Cleveland, OH (US); Brigham and Womens Hospital, Boston, MA (US); The University of Washington, Seattle, WA (US)

( * ) Notice: Subject to any disclaimer, the term of this patent is extended or adjusted under 35 U.S.C. 154(b) by 0 days.

(21) Appl. No.: 13/145,795

(22) PCT Filed: Jan. 22, 2010

(86) PCT No.: PCT/US2010/021700
§ 371 (c)(1),
(2), (4) Date: Feb. 2, 2012

(87) PCT Pub. No.: WO2010/085586
PCT Pub. Date: Jul. 29, 2010

(65) Prior Publication Data
US 2012/0122117 A1    May 17, 2012

Related U.S. Application Data

(60) Provisional application No. 61/146,867, filed on Jan. 23, 2009.

(51) Int. Cl.
*G01N 33/53*    (2006.01)
*G01N 31/00*    (2006.01)

(52) U.S. Cl. ............ 435/7.21; 435/7.1; 436/1; 436/501; 436/518; 424/9.1; 424/520; 422/1; 422/430; 530/300; 530/350

(58) Field of Classification Search .................. None
See application file for complete search history.

(56) References Cited

U.S. PATENT DOCUMENTS

| | | |
|---|---|---|
| 2004/0115745 A1 | 6/2004 | Diamandis et al. |
| 2005/0048574 A1 | 3/2005 | Kantor et al. |
| 2007/0225206 A1 | 9/2007 | Ling et al. |

OTHER PUBLICATIONS

Jamal, et al., "Increased Expression of Human Type IIa Secretory Phospholipase A2 Antigen in Arthritic Synovium", Ann Rheum Dis., Sep. 1998, vol. 57(9), pp. 550-558.
Leistad, et al., "Presence of Secretory Group IIa and V phospolipase A2 and Cytosolic Group Iva Phospholipase A2 in Chondrocytes from patients with rheumatoid arthritis", Clin. Chem. Lab Med., Jun. 2004, vol. 42(6), pp. 602-610.
Lucas, et al., "Distinguishing Phospholipase A2 Types in Biological Samples by employing Group-Specific Assays in the Presence of Inhibitors, Prostaglandins & Other Lipid Mediators", Sep. 2005, vol. 77(1-4), pp. 235-248.

*Primary Examiner* — Lisa Cook
(74) *Attorney, Agent, or Firm* — Tarolli, Sundheim, Covell & Tummino LLP

(57) ABSTRACT

The present invention relates to the use of protein expression profiles of sPLA2 isoforms with clinical relevance to osteoarthritis (OA). In particular, the invention provides methods for diagnosing OA or determining risk factors for development of OA based on expression of sPLA2-IIA.

26 Claims, 3 Drawing Sheets

SECRETED PHOSPHOLIPASE A2 BIOMARKERS FOR ARTHRITIS

This application corres. to PCT/US2010/021700, filed Jan. 22, 2010, which claims priority to U.S. Provisional Patent Application Ser. No. 61/146,867, filed on Jan. 23, 2009, the entire disclosure of which is incorporated herein by reference.

BACKGROUND OF THE INVENTION

Osteoarthritis (OA) is a progressive joint disease, which is characterized by the breakdown of joint cartilage. It may affect one or more joints in the body, including those of the fingers, neck, shoulder, hips, knees, lower spine region, and feet. OA can cause pain and severely impair mobility and lower extremity function (E. Bagge et al., Age Ageing, 1992, 21: 160-167; D. Hamerman, Ann. Rheum. Dis., 1995, 54: 82-85; J. Jordan et al., J. Rheumatol., 1997, 24: 1344-1349; S. M. Ling and J. M. Bathon, J. Am. Geriatr. Soc., 1998, 46: 216-225), which can lead to disability and difficulty maintaining independence (A. A. Guccione et al., Am. J. Public Health, 1994, 84: 351-358; M. A Gignac et al., J. Gerontol. B: Psychol. Sci. Soc. Sci., 2000, 55: 362-372; M. C. Corti and C. Rignon, Aging Clin. Exp. Res., 2003, 15: 359-363). OA is associated with aging: the prevalence of radiographic osteoarthritis is less than 1% in people under 30 years of age but, with increasing age, the prevalence rises sharply and was found to be approximately 80% in individuals over 65 (R. C. Lawrence et al., J. Rheumatol., 1989, 16: 427-441; E. Bagge and P. Brooks, Drugs Aging, 1995, 7: 176-183; N. J. Manek and N. E. Lane, Am. Fam. Physician., 2000, 61: 1795-1804). Despite being a condition that causes most problems to populations after retirement age, OA is also rated the highest cause of work loss in the U.S. and Europe. In addition to age, risk factors known to be associated with OA include obesity, traumatic injury and overuse due to sports or occupational stresses. However, the precise etiology of osteoarthritis is still unknown.

Currently, diagnosis of OA is typically based upon radiological examination as well as clinical observations including localized tenderness, use-related pain, bony or soft tissue swelling, joint instability, limited joint function, muscle spasm, and crepitus (i.e., cracking or grinding sensation). While the diagnosis of OA is often suggested on physical examination, radiographic evaluation is generally used to confirm the diagnosis or assess the severity of the disease. The radiographic hallmarks of OA include non-uniform joint space loss, osteophyte formation, cyst formation, and subchondral sclerosis. While these characteristic features are generally present in X-ray images of "severe" or "late" OA, patients with "early" OA may not show radiographic evidence of bony changes, joint space narrowing and/or osteophytosis, making the diagnosis unclear or difficult to establish. In the absence of a reliable diagnosis, physicians cannot intervene early in the course of the disease, i.e. before signs of joint destruction arise. Magnetic resonance imaging (MRI) is used for delineating articular cartilage morphology and composition, particularly in large joints such as the knee, and can reveal cartilage defects and thinning regions of the joint not visible with radiography (K. Ott and J. Montes-Lucero, Radiol. Technol., 2002, 74: 25-42; F. Eckstein and C. Glaser, Semin. Mucculoskelet. Radiol., 2004, 8: 329-353; G. A. Tung, Med. Health R. I., 2004, 87: 172-175). However, recent studies indicate that MRI may not be very useful in diagnosing OA, due to the frequent incidence of meniscal tears, which may appear both in the presence or absence of knee pain and/or other symptoms of osteoarthritic disease (M. Englund, et al., The New England Journal of Medicine, 2008, 359; 11: 1108-1115).

An additional diagnostic method for OA is arthroscopy, in which a small incision in the patient's skin is made and fiber optic instruments are inserted into the joint. This procedure allows the visualization of the interior of the joint through this very small incision rather than a large incision needed for surgery. However, this technique is invasive, expensive, and may lead to additional pain in the joint. Therefore, alternative, less costly and invasive diagnostic procedures are desirable.

There is currently no cure for OA, and available osteoarthritis therapies are directed at the symptomatic relief of pain, and at improving and maintaining joint function. Furthermore, in the context of the recent withdrawals of COX-2 inhibitors, physicians are even more limited in their choice of treatments for OA. The demand for disease-modifying drugs for OA has grown considerably as awareness of the profound social and economic impact of this prevalent and debilitating disorder has become widespread. However, clinical trials of such drugs rely on the assessment of changes in joint space observed using plain X-rays (S. A. Mazzuca et al., Osteoarthritis and Cartilage, 1997, 5: 217-226). Since changes caused by articular cartilage loss are small (1-2 mm per year), a minimum of one year is required before sufficient changes have occurred to be detectable and, therefore, before a drug's efficacy can be assessed.

Clearly, there is a great need for biological markers of OA and OA progression. In particular, biomarkers that would allow reliable diagnosis and monitoring in the early stages of the disease and permit early intervention to potentially prevent pain and long-term disability are highly desirable. Also needed are biomarkers and design assay systems that could evaluate the efficacy of disease-modifying OA drugs in a time frame significantly shorter than the year currently required for assessment of radiological changes.

SUMMARY OF THE INVENTION

The present invention relates to the use of expression profiles of secreted phosopholipase A2 (sPLA2) isoforms with clinical relevance to arthritis, e.g., OA and rheumatoid arthritis (RA). The sPLA2 expression profiles described herein provide novel correlates of disease activity for arthritis. In particular, the invention provides methods for diagnosing OA or determining risk factors for development of OA based on an expression pattern of sPLA2 isoforms. Compared to existing methods of diagnosis, the analysis of expression of sPLA2 isoforms disclosed herein (e.g., expression of sPLA2-IIA and one or more other isoforms of sPLA2) allows accurate diagnosis of OA and OA progression, and provides a reliable basis for the selection of appropriate therapeutic regimens.

In one aspect, the present invention provides methods of determining the prognosis, presence of, risk for, progression or abatement of OA in a subject. The methods include, for example, providing a biological sample from a subject; evaluating expression or activity of a first isoform of secretory phospholipase A2 (sPLA2), wherein the first isoform is sPLA2 Group IIA (sPLA2-IIA) in the biological sample; and evaluating expression or activity of at least one other isoform of sPLA2. The at least one other isoform includes, for example, one or more of sPLA2-IB, sPLA2-IIC, sPLA2-IID, sPLA2-IIE, sPLA2-IIF, sPLA2-III, sPLA2-X, sPLA2-V, sPLA2-XIIA, or sPLA2-XIIB in the biological sample; and correlating expression or activity of the sPLA2 isoforms with presence, risk, prognosis, progression, or abatement of OA.

In some embodiments, expression or activity of sPLA2 isoforms is evaluated relative to one or more controls.

In some embodiments, expression or activity of sPLA2 isoforms in a subject is evaluated at a first timepoint relative to one or more later timepoints. In some embodiments, an increase in expression or activity of sPLA2-IIA over time and a lack of increase in expression or activity of at least one other sPLA2 isoform over time is indicative of OA disease progression. In some embodiments, a lack of increase in expression or activity f sPLA2-IIA over time (e.g., stable levels of sPLA2-IIA, or decreased levels over time) is indicative of OA disease abatement. sPLA2 expression or activity in a subject can be evaluated at intervals of days, weeks, months, or years. In some embodiments, sPLA2 expression or activity is evaluated at a first timepoint and a second timepoint is one week, two weeks, one month, three months, six months, or one year later. In some embodiments, sPLA2 expression or activity is evaluated in a subject receiving therapy for OA. The pattern of sPLA2 isoform expression or activity (e.g., over time) can be indicative of the subject's response to therapy. Elevated expression or activity of sPLA2-IIA, (e.g., elevated two, three, four or five times relative to expression of sPLA2-IIA in a subject that does not have osteoarthritis) in conjunction with a lack of elevated expression or activity of at least one other isoform of sPLA2, is correlated with the presence, risk, prognosis, progression, or abatement of arthritis.

In some embodiments, the biological sample comprises synovial fluid, blood, a blood product, urine, or saliva from the subject. In some embodiments, the biological sample comprises synovial fluid.

In some embodiments, expression of sPLA2-IIA polypeptides is evaluated (e.g., with an antibody). In some embodiments, the antibody specifically binds to sPLA2-IIA. In some embodiments, expression of sPLA2-IIA polypeptides is evaluated using an immunoassay (e.g., a time-resolved fluorescence immunoassay). In some embodiments, expression of sPLA2-IIA nucleic acids (e.g., mRNA) is evaluated. In some embodiments, sPLA2-IIA activity is evaluated (e.g., using an isoform-specific inhibitor or substrate).

In some embodiments, expression of polypeptides of the at least one other sPLA2 isoform is evaluated (e.g., with an antibody). In some embodiments, the antibody specifically binds to the at least one other sPLA2 isoform. In some embodiments, expression of the at least one other sPLA2 isoform polypeptides is evaluated using an immunoassay (e.g., a time-resolved fluorescence immunoassay). In some embodiments, expression of the nucleic acids (e.g., mRNA) of the at least one other sPLA2 isoform is evaluated. In some embodiments, activity of the at least one other sPLA2 isoform is evaluated (e.g., using an isoform-specific inhibitor or substrate).

In some embodiments, expression or activity of at least two, three, four, five, six, seven, eight, or nine of the other sPLA2 isoforms is evaluated. In some embodiments, expression or activity of at least three of the other sPLA2 isoforms is evaluated. In some embodiments, expression or activity of at least four of the other sPLA2 isoforms is evaluated. In some embodiments, expression or activity of two or three of sPLA2-IIF, sPLA2-III, and sPLA2-V are evaluated.

Various types of controls can be used in the methods. In some embodiments, the control comprises a sample lacking detectable expression or activity of sPLA2-IIA. In some embodiments, the control comprises a sample from a subject that does not have osteoarthritis. In some embodiments, the control comprises a sample from a subject that has been diagnosed with arthritis. In some embodiments, the control comprises a sample from a subject that has been diagnosed with osteoarthritis.

In some embodiments, the subject is a human. In some embodiments, the subject is a subject suffering from joint pain. In some embodiments, the subject is suspected of having arthritis. In some embodiments, the subject is suspected of having osteoarthritis.

In some embodiments, the method further comprises selecting a therapy for the subject based on the determining. In some embodiments, the method further comprises administering the selected therapy.

In another aspect, the present invention also provides kits for determining presence, risk, prognosis, progression, or abatement of OA in a subject. The kits can include a reagent that specifically detects expression or activity of sPLA2-IIA and a reagent for detecting at least one other sPLA2 isoform in a sample from a subject and instructions for using the reagent to determine whether a subject has, or is at risk for, arthritis. In some embodiments, a kit comprises at least one reagent that detects sPLA2-IIA polypeptides. In some embodiments, the at least one reagent comprises an antibody that specifically binds to sPLA2-IIA polypeptides. In some embodiments, a kit comprises substrates or inhibitors specific for various sPLA2 isoforms, which allow one to evaluate the presence and activity of the isoforms.

In another aspect, the present invention provides methods of distinguishing the presence of OA from the presence of RA in a subject. In some embodiments, the presence of rheumatoid arthritis is determined in a subject. The methods include, for example, providing a biological sample from a subject, evaluating expression or activity of a first isoform of secretory phospholipase A2 (sPLA2) in the biological sample, wherein the first isoform is sPLA2 Group HA (sPLA2-IIA); evaluating expression or activity of at least one other isoform of sPLA2 in the biological sample, and correlating expression or activity of sPLA2-IIA and the at least one other isoform of sPLA2 with a risk for, or presence of, rheumatoid arthritis. In some embodiments, elevated sPLA2-IIA and elevated expression or activity of a second isoform (e.g., one or more of sPLA2-V, sPLA2-IB, sPLA2-III, or sPLA2-XIIA) is indicative of RA.

Details of certain embodiments of the present invention are set forth in the accompanying drawings and the description below. Other features, objects, and advantages of the present invention will be apparent from the description and drawing, and from the claims. All cited patents, and patent applications and references (including references to public sequence database entries) are incorporated by reference in their entireties for all purposes.

DEFINITIONS

Figure 1:
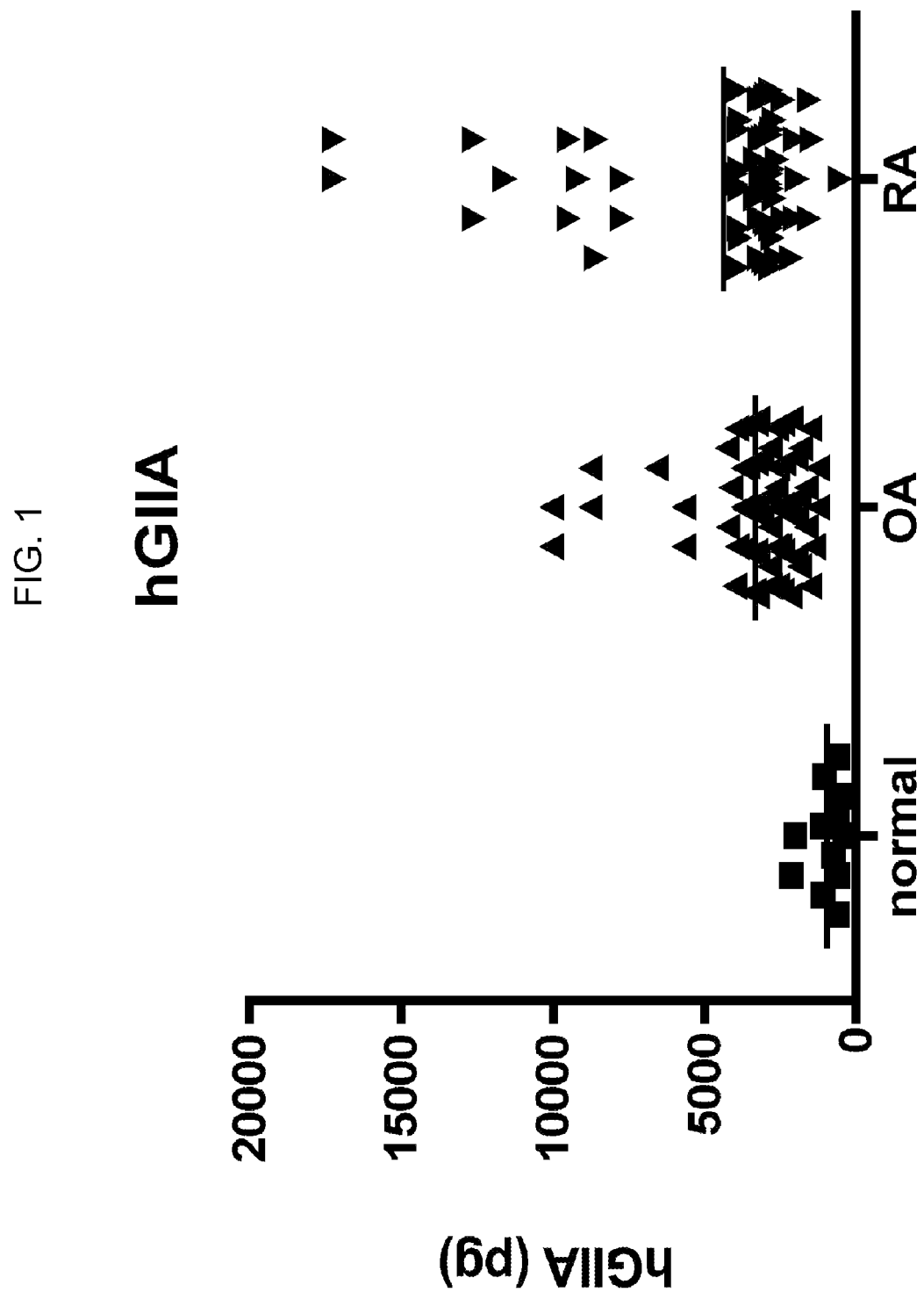
FIG. 1: Exemplary data demonstrating the quantitation by time resolved fluorescent immunoassay of human sPLA2-IIA levels in normal, osteoarthritis (OA), and rheumatoid arthritis (RA) human patients.

Throughout the specification, several terms are employed that are defined in the following paragraphs.

As used herein, the term "antibody" refers to any immunoglobulin, whether natural or wholly or partially synthetically produced. All derivatives thereof which maintain specific binding ability are also included in the term. The term also covers any protein having a binding domain which is homologous or largely homologous to an immunoglobulin binding domain. Such proteins may be derived from natural sources, or partly or wholly synthetically produced. An antibody may be monoclonal or polyclonal. An antibody may be a member of any immunoglobulin class, including any of the human classes: IgG, IgM, IgA, IgD, and IgE. As used herein, the terms "antibody fragment" or "characteristic portion of an antibody" are used interchangeably and refer to any derivative of an antibody which is less than full-length. In general, an antibody fragment retains at least a significant portion of the full-length antibody's specific binding ability. Examples of antibody fragments include, but are not limited to, Fab, Fab', F(ab')2, scFv, Fv, dsFv diabody, and Fd fragments. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains which are linked together, for example, by disulfide linkages. An antibody fragment may optionally comprise a multimolecular complex. A functional antibody fragment typically comprises at least about 50 amino acids and more typically comprises at least about 200 amino acids.

The terms "array", "micro-array", and "biochip" are used herein interchangeably. They refer to an arrangement, on a substrate surface, of hybridizable array elements, preferably, multiple nucleic acid molecules of known sequences. Each nucleic acid molecule is immobilized to a discrete spot (i.e., a defined location or assigned position) on the substrate surface. The term "micro-array" more specifically refers to an array that is miniaturized so as to require microscopic examination for visual evaluation.

The term "biological sample" is used herein in its broadest sense. A biological sample may be obtained from a subject (e.g., a human) or from components (e.g., tissues) of a subject. The sample may be of any biological tissue or fluid with which biomarkers of the present invention may be assayed. Frequently, the sample will be a "clinical sample", i.e., a sample derived from a patient. Such samples include, but are not limited to, bodily fluids which may or may not contain cells, e.g., blood, urine, synovial fluid, saliva, and joint fluid; tissue or fine needle biopsy samples, such as from bone or cartilage; and archival samples with known diagnosis, treatment and/or outcome history. Biological samples may also include sections of tissues such as frozen sections taken from histological purposes. The term biological sample also encompasses any material derived by processing the biological sample. Derived materials include, but are not limited to, cells (or their progeny) isolated from the sample, proteins or nucleic acid molecules extracted from the sample. Processing of the biological sample may involve one or more of: filtration, distillation, extraction, concentration, inactivation of interfering components, addition of reagents, and the like.

The terms "compound" and "agent" are used herein interchangeably. They refer to any naturally occurring or non-naturally occurring (i.e., synthetic or recombinant) molecule, such as a biological macromolecule (e.g., nucleic acid, polypeptide or protein), organic or inorganic molecule, or an extract made from biological materials such as bacteria, plants, fungi, or animal (particularly mammalian, including human) cells or tissues. The compound may be a single molecule or a mixture or complex of at least two molecules.

The term "computer readable medium" refers to any device or system for storing or providing information (e.g., data and instructions) to a computer processor. Examples of computer readable media include, but are not limited to, DVDs, CDs, hard disk drives, magnetic tape and servers for streaming media over networks.

In the context of the present invention, the term "control sample" is a sample used for comparison to a test sample. In some embodiments, a control sample refers to one or more biological samples isolated from an individual or group of individuals that are normal (i.e., healthy). A control sample can also refer to a biological sample isolated from a patient or group of patients diagnosed with a specific OA subtype (i.e., subtype I or subtype II) or a specific stage of OA (e.g., early OA or late OA). The term "control sample" (or "control") can also refer to the compilation of data derived from samples of one or more individuals classified as normal, or one or more individuals diagnosed with OA, a specific OA subtype or a specific stage of OA, or one or more individuals having undergone treatment of OA. In the context of analysis of sPLA2-IIA expression, a control sample can be a sample that has a known level of sPLA2-IIA (e.g., a lack of detectable sPLA2-IIA expression, or an elevated level of sPLA2-IIA expression known to be indicative of OA).

As used herein, the term "diagnosis" refers to a process aimed at determining if an individual is afflicted with a disease or ailment. In the context of the present invention, "diagnosis of OA" refers to a process aimed at one or more of: determining if an individual is afflicted with OA, identifying an OA subtype (i.e., subtype I or subtype II), and determining the stage of the disease (e.g., early OA or late OA).

As used herein, the term "differentially expressed biomarker" refers to a biomarker whose level of expression is different in a subject (or a population of subjects) afflicted with OA relative to its level of expression in a healthy or normal subject (or a population of healthy or normal subjects). The term also encompasses a biomarker whose level of expression is different for a different disease subtype (i.e., OA subtype I and OA subtype II). The term further encompasses a biomarker whose level of expression is different at different stages of the disease (e.g., mild or early OA, severe or late OA). Differential expression includes quantitative, as well as qualitative, differences in the temporal or cellular expression pattern of the biomarker. As described in greater details below, a differentially expressed biomarker, alone or in combination with other differentially expressed biomarkers, is useful in a variety of different applications in diagnostic, staging, therapeutic, drug development and related areas. The expression patterns of the differentially expressed biomarkers disclosed herein can be described as a fingerprint or a signature of OA, OA subtype, OA stage and OA progression. They can be used as a point of reference to compare and characterize unknown samples and samples for which further information is sought. The term "decreased level of expression", as used herein, refers to a decrease in expression of at least 10% or more, for example, 20%, 30%, 40%, or 50%, 60%, 70%, 80%, 90% or more, or a decrease in expression of greater than 1-fold, 2-fold, 3-fold, 4-fold, 5-fold, 10-fold, 50-fold, 100-fold or more as measured by one or more methods described herein. The term "increased level of expression", as used herein, refers to an increase in expression of at least 10% or more, for example, 20%, 30%, 40%, or 50%, 60%, 70%, 80%, 90% or more or an increase in expression of greater than 1-fold, 2-fold, 3-fold, 4-fold, 5-fold, 10-fold, 50-fold, 100-fold or more as measured by one or more methods, such as method described herein.

As used herein, the term "effective amount" refers to an amount of a compound or agent that is sufficient to fulfill its intended purpose(s). In the context of the present invention, the purpose(s) may be, for example: to modulate the expression of at least one inventive biomarker; and/or to delay or prevent the onset of OA; and/or to slow down or stop the progression, aggravation, or deterioration of the symptoms of OA; and/or to bring about amelioration of the symptoms of OA, and/or to cure OA.

The term "hybridizing" refers to the binding of two single stranded nucleic acids via complementary base pairing. The term "specific hybridization" refers to a process in which a nucleic acid molecule preferentially binds, duplexes, or hybridizes to a particular nucleic acid sequence under stringent conditions (e.g., in the presence of competitor nucleic acids with a lower degree of complementarity to the hybridizing strand). In certain embodiments of the present invention, these terms more specifically refer to a process in which a nucleic acid fragment (or segment) from a test sample preferentially binds to a particular probe and to a lesser extent or not at all, to other probes, for example, when these probes are immobilized on an array.

As used herein, the term "indicative of OA", when applied to a biomarker, refers to an expression pattern or profile which is diagnostic of OA, OA subtype, or a stage of OA such that the expression pattern is found significantly more often in patients with the disease, disease subtype, or a stage of the disease than in patients without the disease or another subtype or stage of the disease (as determined using routine statistical methods setting confidence levels at a minimum of 95%). Preferably, an expression pattern which is indicative of OA is found in at least 60% of patients who have the disease and is found in less than 10% of subjects who do not have the disease. More preferably, an expression pattern which is indicative of OA is found in at least 70%, at least 75%, at least 80%, at least 85%, at least 90%, at least 95% or more in patients who have the disease and is found in less than 10%, less than 8%, less than 5%, less than 2.5%, or less than 1% of subjects who do not have the disease.

The terms "labeled", "labeled with a detectable agent" and "labeled with a detectable moiety" are used herein interchangeably. These terms are used to specify that an entity (e.g., a probe) can be visualized, for example, following binding to an other entity (e.g., a polynucleotide or polypeptide). Preferably, the detectable agent or moiety is selected such that it generates a signal which can be measured and whose intensity is related to the amount of bound entity. In array-based methods, the detectable agent or moiety is also preferably selected such that it generates a localized signal, thereby allowing spatial resolution of the signal from each spot on the array. Methods for labeling polypeptides or polynucleotides are well-known in the art. Labeled polypeptides or polynucleotides can be prepared by incorporation of or conjugation to a label, that is directly or indirectly detectable by spectroscopic, photochemical, biochemical, immunochemical, electrical, optical, or chemical means. Suitable detectable agents include, but are not limited to, various ligands, radionuclides, fluorescent dyes, chemiluminescent agents, microparticles, enzymes, colorimetric labels, magnetic labels, and haptens. Detectable moieties can also be biological molecules such as molecular beacons and aptamer beacons.

The terms "normal" and "healthy" are used herein interchangeably. They refer to an individual or group of individuals who have not shown any OA symptoms, including joint pain, and have not been diagnosed with cartilage injury or OA. Preferably, said normal individual (or group of individuals) is not on medication affecting OA and has not been diagnosed with any other disease. In certain embodiments, normal individuals have similar sex, age, body mass index as compared with the individual from which the sample to be tested was obtained. The term "normal" is also used herein to qualify a sample isolated from a healthy individual.

The terms "nucleic acid molecule" and "polynucleotide" are used herein interchangeably. They refer to a deoxyribonucleotide or ribonucleotide polymer in either single- or double-stranded form, and unless otherwise stated, encompass known analogs of natural nucleotides that can function in a similar manner as naturally occurring nucleotides. The terms encompass nucleic acid-like structures with synthetic backbones, as well as amplification products.

The terms "osteoarthritis stage" and "osteoarthritis phase" are used herein interchangeably and refer to the degree of advancement or progression of the disease. The present invention provides a means for determining the stage of the disease. In particular, the methods provided herein allows detection of "mild" or "early" OA, and of "severe" or "late" OA. Other staging systems known in the art include, for example, that developed by Marshall (W. Marshall, J. Rheumatol., 1996, 23: 582-584).

The term "probe", as used herein, refers to a nucleic acid molecule of known sequence, which can be a short DNA sequence (i.e., an oligonucleotide), a PCR product, or mRNA isolate. Probes are specific DNA sequences to which nucleic acid fragments from a test sample are hybridized. Probes specifically bind to nucleic acids of complementary or substantially complementary sequence through one or more types of chemical bonds, usually through hydrogen bond formation.

The terms "protein", "polypeptide", and "peptide" are used herein interchangeably, and refer to amino acid sequences of a variety of lengths, either in their neutral (uncharged) forms or as salts, and either unmodified or modified by glycosylation, side chain oxidation, or phosphorylation. In certain embodiments, the amino acid sequence is the full-length native protein. In other embodiments, the amino acid sequence is a smaller fragment of the full-length protein. In still other embodiments, the amino acid sequence is modified by additional substituents attached to the amino acid side chains, such as glycosyl units, lipids, or inorganic ions such as phosphates, as well as modifications relating to chemical conversion of the chains, such as oxidation of sulfhydryl groups. Thus, the term "protein" (or its equivalent terms) is intended to include the amino acid sequence of the full-length native protein, subject to those modifications that do not change its specific properties. In particular, the term "protein" encompasses protein isoforms, i.e., variants that are encoded by the same gene, but that differ in their pI or MW, or both. Such isoforms can differ in their amino acid sequence (e.g., as a result of alternative splicing or limited proteolysis), or in the alternative, may arise from differential post-translational modification (e.g., glycosylation, acylation, phosphorylation).

The term "protein analog", as used herein, refers to a polypeptide that possesses a similar or identical function as the full-length native protein but need not necessarily comprise an amino acid sequence that is similar or identical to the amino acid sequence of the protein, or possesses a structure that is similar or identical to that of the protein. Preferably, in the context of the present invention, a protein analog has an amino acid sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the amino acid sequence of the full-length native protein.

The term "protein fragment", as used herein, refers to a polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of a second polypeptide. The fragment of a marker protein may or may not possess a functional activity of the full-length native protein.

As used herein, the term "a reagent that specifically detects expression levels" refers to one or more reagents used to detect the expression level of one or more biomarkers (e.g., a specific sPLA2 isoform, such as sPLA2-IIA, a nucleic acid molecule comprising a polynucleotide sequence coding for an sPLA2 isoform, or a polynucleotide that hybridizes with at least a portion of the nucleic acid molecule). Examples of suitable reagents include, but are not limited to, antibodies capable of specifically binding to a marker protein of interest, nucleic acid probes capable of specifically hybridizing to a polynucleotide sequence of interest, or PCR primers capable of specifically amplifying a polynucleotide sequence of interest. The term "amplify" is used herein in the broad sense to mean creating/generating an amplification product. "Amplification", as used herein, generally refers to the process of producing multiple copies of a desired sequence, particularly those of a sample. A "copy" does not necessarily mean perfect sequence complementarity or identity to the template sequence.

The term "subject", and "individual" are used herein interchangeably. They refer to a human or another mammal (e.g., primate, dog, cat, goat, horse, pig, mouse, rat, rabbit, and the like), that can be afflicted with osteoarthritis, but may or may not have the disease. In many embodiments, the subject is a human being.

The term "subject suspected of having OA" refers to a subject that presents one or more symptoms indicative of OA (e.g., joint pain, localized tenderness, bony or soft tissue swelling, joint instability, crepitus) or that is being screened for OA (e.g., during a routine physical examination). A subject suspected of having OA may also have one or more risk factors (e.g., age, obesity, traumatic injury, overuse due to sports or occupational stresses, family history). The term encompasses individuals who have not been tested for OA as well as individuals who have received an initial diagnosis (e.g., based on radiological examination) but for whom the stage of OA is not known, and/or for whom OA subtype is not known.

The term "system" and "biological system" are used herein interchangeably. A system may be any biological entity that can express or comprise at least one inventive biomarker. In the context of the present invention, in vitro, in vivo, and ex vivo systems are considered; and the system may be a cell, a biological fluid, a biological tissue, or an animal. For example, a system may originate from a living subject (e.g., it may be obtained by drawing blood, or by performing needle biopsy), or from a deceased subject (e.g., it may be obtained at autopsy).

The term "treatment" is used herein to characterize a method that is aimed at (1) delaying or preventing the onset of OA; or (2) slowing down or stopping the progression, aggravation, or deterioration of the symptoms of the condition; or (3) bringing about ameliorations of the symptoms of the condition; or (4) curing the condition. A treatment may be administered prior to the onset of the disease, for a prophylactic or preventive action. It may also be administered after initiation of the disease, for a therapeutic action.

DETAILED DESCRIPTION OF CERTAIN PREFERRED EMBODIMENTS

As mentioned above, the present invention relates to methods and compositions for the diagnosis, characterization, and staging of arthritis, e.g., OA or RA. In particular, the present invention provides methods for determining whether a subject has, or is at risk for, arthritis by evaluating expression of sPLA2 isoforms that correlate with OA, OA subtype, and OA progression. In particular embodiments, the methods include the evaluation of expression of sPLA2-IIA and at least one other isoform of sPLA2.

sPLA2 Biomarkers

Secreted phospholipases A2 hydrolyze membrane phospholipids to produce free fatty acids and lysophospholipids. sPLA2 family members, which are disulfide rich polypeptides, typically of 14-19 kDa, are highly diverse. At least ten different enzymatically active mammalian isoforms of sPLA2 are known. The present invention encompasses the discovery that expression of certain sPLA2 isoforms correlates with the presence of certain types of arthritis, e.g., OA or RA. In particular, it has been discovered that isolated elevated expression of sPLA2-IIA and lack elevated expression of other sPLA2 isoforms is associated with the presence of OA. By contrast, elevated expression of sPLA2-IIA and other isoforms of sPLA2 is associated with RA. Accordingly, analysis of expression or activity of sPLA2 isoforms can be employed to evaluate risk for OA or RA, detect the presence of OA or RA, and/or monitor progression or abatement of OA or RA.

Several sPLA2s, including IIA and V share a common three dimensional structure based on structural data and sequence alignment. All sPLA2s share the common structural feature of a ~15 Angstrom deep active slot where a single phospholipid molecule binds to position the enzyme-susceptible ester next to the catalytic residues. See Lambeau et al. "Biochemistry and Physiology of Mammalian Secreted Phospholipases A2," *Annu. Rev. Biochem.* (2008) 77:495-520. Several sPLA2s share high levels of sequence homology. For example, human sPLA2-IIA and sPLA-V share about 40% amino acid sequence identity.

Although sPLA2s exhibit regions of high sequence homology to one another, specific isoforms of sPLA2s can be detected by antibodies that preferentially bind to regions that are not highly conserved (see e.g., Nevalainen et al., Biochem. Biophys. Acta. 1733:210-223, 2005). To give but one example, interfacial residues have been modeled in a three dimensional manner for several sPLA2 isoforms. Several of the residues that make up the interfacial region of the protein are distinct between one isoform and another (Winget, et al. *Biochimica et Biophysica Acta;* 1761; 2006; 1260-1269). Antibodies may discriminate between an sPLA2 isoform (e.g., sPLA2-IIA) and others (e.g., sPLA2-V).

The terms "sPLA2-IIA polypeptide," "sPLA2-IIA protein" and "sPLA2-IIA" are used inter-changeably herein and encompass naturally-occurring sPLA2-IIA sequences and sPLA2-IIA variants. sPLA2-IIA polypeptides suitable for the invention may be isolated from a variety of sources, such as from human or non-human (e.g., mouse) tissues, or prepared by recombinant or synthetic methods.

As non-limiting examples, a nucleotide sequence encoding a human sPLA2-IIA polypeptide is shown in Table 1. An amino acid sequence of a human sPLA-IIA is shown in Table 2.

TABLE 1

Human sPLA2 Isoform IIA (hPLA2-IIA) nucleotide sequence (GenBank Accession # NM_000300)

(SEQ ID NO: 1)

```
  1 gaaggaaaaa gagcaacaga tccagggagc attcacctgc cctgtctcca aacagccttg 61 tgcctcacct accccaacc tcccagaggg agcagctatt taaggggagc aggagtgcag 121 aacaaacaag acggcctggg gatacaactc tggagtcctc tgagagagcc accaaggagg 181 agcaggggag cgacggccgg ggcagaagtt gagaccaccc agcagaggag ctaggccagt 241 ccatctgcat ttgtcaccca agaactctta ccatgaagac cctcctactg ttggcagtga 301 tcatgatctt tggcctactg caggcccatg ggaatttggt gaatttccac agaatgatca 361 agttgacgac aggaaaggaa gccgcactca gttatggctt ctacgctgc cactgtggcg 421 tgggtggcag aggatccccc aaggatgcaa cggatcgctg ctgtgtcact catgactgtt 481 gctacaaacg tctggagaaa cgtggatgtg gcaccaaatt tctgagctac aagtttagca 541 actcggggag cagaatcacc tgtgcaaaac aggactcctg cagaagtcaa ctgtgtgagt 601 gtgataaggc tgctgccacc tgttttgcta gaaacaagac gacctacaat aaaaagtacc 661 agtactattc aataaacac tgcagaggga caccctcg ttgctgagtc ccctcttccc 721 tggaaacctt ccacccagtg ctgaatttcc ctctctcata ccctccctcc ctacctaac 781 caagttcctt ggccatgcag aaagcatccc tcacccatcc tagaggccag gcaggagccc 841 ttctataccc acccagaatg agacatccag cagatttcca gccttctact gctctcctcc 901 acctcaactc cgtgcttaac caaagaagct gtactccggg gggtctcttc tgaataaagc 961 aattagcaaa aaaaaaaaa aaaaaaaaa aaaaaaa
```

TABLE 2

Human sPLA2-IIA polypeptide sequence (GenBank Accession # NP_000291)

(SEQ ID NO: 2)

MKTLLLLAVIMIFGLLQAHGNLVNF<u>HRMIK</u>LTTGKEAALSYGFYGCHCG

V*G*GRGSP<u>K</u>DATDRCCVTH*D*CCYKRLEKRGCGTKFLSYKFSNSGS<u>RITCA</u>

<u>KQDSCRSQLCECDKAAATCFARN</u>KTTYNKKYQYYSNK<u>H</u>CRGSTPRC

The first 20 amino acids may constitute the prepeptide (bold). H47 (bold) may be an important amino acid from the catalytic site. G29 and D48 (bold italic) may bind the calcium ion which is central for catalytic activity. Certain basic patches that may be involved in interacting with lipid vesicles are underlined.

In some embodiments, expression of sPLA2-IIA is compared to expression of other sPLA2 isoforms. Sequences of other sPLA2 isoforms are known. As a non-limiting example, a nucleotide sequence encoding a human sPLA2 Group V polypeptide is shown in Table 3. An amino acid sequence of a human sPLA2 Group V polypeptide is shown in Table 4.

TABLE 3

Human sPLA2 Group V (hPLA2-V) nucleotide sequence (GenBank Accession # NM_000929)

(SEQ ID NO: 3)

```
  1 cagggttcta cccggctggg tccaggcaga agtttttcct ccccacctcc gggtttgtcc 61 tcatcatcgg tcactcccat tcacagcttt aagattctgg aggccaagaa tttgactccc 121 cccggatcca tggtctgtgg ataccaatgt tccgactgga gacggggagc ccgcgagacc 181 cgggtctcca gggtctgccc aaggaagttg ctcatgggag cagacctcta gagcaggatt 241 tgaggccagg ccaaagagaa ccccagagat gaaaggcctc ctcccactgg cttggttcct 301 ggcttgtagt gtgcctgctg tgcaaggagg cttgctggac ctaaaatcaa tgatcgagaa 361 ggtgacaggg aagaacgccc tgacaaacta cggcttctac ggctgttact gcggctgggg 421 cggccgagga acccccaagg atggcaccga ttggtgctgt tgggcgcatg accactgcta 481 tgggcggctg gaggagaagg gctgcaacat tcgcacacag tcctacaaat acagattcgc 541 gtggggcgtg gtcacctgcg agcccgggcc cttctgccat gtgaacctct gtgcctgtga
```

TABLE 3-continued

| | | | | | | |
|---|---|---|---|---|---|---|
| 601 | ccggaagctc | gtctactgcc | tcaagagaaa | cctacggagc | tacaacccac | agtaccaata |
| 661 | ctttcccaac | atcctctgct | cctaggcctc | cccagcgagc | tcctcccaga | ccaagacttt |
| 721 | tgttctgttt | ttctacaaca | cagagtactg | actctgcctg | gttcctgaga | gaggctccta |
| 781 | agtcacagac | ctcagtcttt | ctcgaagctt | ggcggacccc | cagggccaca | ctgtaccctc |
| 841 | cagcgagtcc | caggagagtg | actctggtca | taggacttgg | tagggtccca | gggtccctag |
| 901 | gcctccactt | ctgagggcag | cccctctggt | gccaagagct | ctcctccaac | tcagggttgg |
| 961 | ctgtgtctct | tttcttctct | gaagacagcg | tcctggctcc | agttggaaca | ctttcctgag |
| 1021 | atgcacttac | ttctcagctt | ctgcgatcag | attatcatca | ccaccaccct | ccagagaatt |
| 1081 | tttacgcaag | aagagccaaa | ttgactctct | aaatctggtg | tatgggtatt | aaataaaatt |
| 1141 | cattctcaag | gctaataaaa | accacattgg | cattttcctc | tgctgtgggg | gatcgctggt |
| 1201 | gcctctttct | ctgccactgg | ggcaataaac | ccaaagatgt | ctacattatc | tccgaaacag |
| 1261 | aagggaagat | tagtaaatgc | agggtttttct | gggatgagct | tcaggctttc | tcttgggcta |
| 1321 | atttcttac | accttggggt | cctctccagt | attgggtctc | attcttcctc | gatggggtca |
| 1381 | gggaaagata | actggtgatt | atgccagctt | cagcttccag | gccagagagg | gtggcattca |
| 1441 | aatcccagtg | ctggcttctt | cagctgtgtg | gtcttggacc | cgttactgaa | cctctttgac |
| 1501 | tttcagtctc | tttgagaaat | aaactgtctt | gttccttgca | atgtaaaatg | agacttctaa |
| 1561 | agcccacctt | gatgctgata | tggagaatgc | tgaggttcta | ggatttcaca | cagcaggaat |
| 1621 | tttttttaa | taggtgtcag | ctgtggggtt | tattttttac | aaagtaagga | cattaaaaaa |
| 1681 | accaacccgt | ctatcaattc | ataaaagaaa | ggatgttctg | ataccaagac | tgaaagaaga |
| 1741 | aaggatgtat | tccaaaacaa | aggaacatcc | ttccaagaaa | ggacctatgg | cttctttatt |
| 1801 | ccgacatacc | ccaaaataac | tgcatgataa | ataggtctat | atttaaaaag | ctctagtgtc |
| 1861 | gaatgttttc | aaaataaaat | ttaattttat | gagaaaaaaa | aaaaaaaaaa | a |

TABLE 4

Human sPLA2-V polypeptide sequence (GenBank Accession # NP_000920)

(SEQ ID NO: 4)
MKGLLPLAWFLACSVPAVQGGLLDLKSMIEKVTGKNALTNYGFYGCYCG

WGGRGTPKDGTDWCCWAHDHCYGRLEEKGCNIRTQSYKYRFAWGVVTCE

PGPFCHVNLCACDRKLVYCLKRNLRSYNPQYQYFPNILCS

Human group V sPLA2, like other sPLA2s, has an interfacial binding site (IBS) that is structurally distinct from the catalytic site. The catalytic site is a slot on the protein where a single phospholipid substrate binds to undergo hydrolysis. Since naturally occurring phospholipids have virtually no solubility in water, sPLA2s need to bind to the membrane interface in order to gain access to their substrate. The surface of the protein that surrounds the opening to the catalytic site slot is the IBS. The IBS is composed of several amino acid residues, each of which makes relatively small contributions to the overall binding of the enzyme to the membrane surface. The catalytic site and IBS are independent sites in a functional sense. For example, the sPLA2 can be bound to the membrane interface via its IBS with or without a phospholipid molecule in its catalytic site.

The residues that may constitute the IBS of group V sPLA2 are shown above in the sequence of the protein as boldface residues.

Sequences of additional sPLA2 isoforms are known and publicly available. See, e.g., sPLA2-IB (GenBank Accession #NM_000928), sPLA2-IID (GenBank Accession #NM_012400), sPLA2-IIE (GenBank Accession #AF189279), sPLA2-IIF (UniProtKB/Swiss-Prot #Q9BZM2), sPLA2-III (GenBank Accession #NM_015715), sPLA2-X (GenBank Accession #NM_003561), sPLA2-XIIA (UniProtKB/Swiss-Prot #Q9BZM1), and sPLA2-XIIB-like (UniProtKB/Swiss-Prot #Q9BX93). Exemplary amino acid sequences of other sPLA2 isoforms are shown in Table 5.

TABLE 5

Human sPLA2-IB (GenBank Accession #NM_000928)

(SEQ ID NO: 5)

MKLLVLAVLLTVAAADSGISPRAVWQFRKMIKCVIPGSDPFLEYNNYGC
YCGLGGSGTPVDELDKCCQTHDNCYDQAKKLDSCKFLLDNPYTHTYSYS
CSGSAITCSSKNKECEAFICNCDRNAAICFSKAPYNKAHKNLDTKKYCQS

Human sPLA2-IID (GenBank Accession #NM_012400)

(SEQ ID NO: 6)

MELALLCGLVVMAGVIPIQGGILNLNKMVKQVTGKMPILSYWPYGCHCG
LGGRGQPKDATDWCCQTHDCCYDHLKTQGCSIYKDYYRYNFSQGNIHCS
DKGSWCEQQLCACDKEVAFCLKRNLDTYQKRLRFYWRPHCRGQTPGC

Human sPLA2-IIE (GenBank Accession #AF189279)

(SEQ ID NO: 7)

MKSPHVLVFLCLLVALVTGNLVQFGVMIEKMTGKSALQYNDYGCYCGIG
GSHWPVDQTDWCCHAHDCCYGRLEKLGCEPKLEKYLFSVSERGIFCAGR
TTCQRLTCECDKRAALCFRRNLGTYNRKYAHYPNKLCTGPTPPC

TABLE 5-continued

```
Human sPLA2-IIF (UniProtKB/Swiss-Prot #Q9BZM2)
                                         (SEQ ID NO: 8)
MKKFFTVAILAGSVLSTAHGSLLNLKAMVEAVTGRSAILSFVGYGCYCG
LGGRGQPKDEVDWCCHAHDCCYQELFDQGCHPYVDHYDHTIENNTEIVC
SDLNKTECDKQTCMCDKNMVLCLMNQTYREEYRGFLNVYCQGPTPNCSI
YEPPPEEVTCSHQSPAPPAPP Human sPLA2-III (GenBank Accession #NM_015715)
                                         (SEQ ID NO: 9)
MGVQAGLFGMLGFLGVALGGSPALRWYRTSCHLTKAVPGNPLGYLSFLA
KDAQGLALIHARWDAHRRLQSCSWEDEPELTAAYGALCAHETAWGSFIH
TPGPELQRALATLQSQWEACRALEESPAGARKKRAAGQSGVPGGGHQRE
KRGWTMPGTLWCGVGDSAGNSSELGVFQGPDLCCREHDRCPQNISPLQY
NYGIRNYRFHTISHCDCDTRFQQCLQNQHDSISDIVGVAFFNVLEIPCF
VLEEQEACVAWYWWGGCRMYGTVPLARLQPRTFYNASWSSRATSPTPSS
RSPAPPKPRQKQHLRKGPPHQKGSKRPSKANTTALQDPMVSPRLDVAPT
GLQGPQGGLKPQGARWVCRSFRRHLDQCEHQIGPREIEFQLLNSAQEPL
FHCNCTRRLARFLRLHSPPEVTNMLWELLGTTCFKLAPPLDCVEGKNCS
RDPRAIRVSARHLRRLQQRRHQLQDKGTDERQPWPSEPLRGPMSFYNQC
LQLTQAARRPDRQQKSWSQ Human sPLA2-X (GenBank Accession #NM_003561)
                                         (SEQ ID NO: 10)
MGPLPVCLPIMLLLLLPSLLLLLLLPGPGSGEASRILRVHRRGILELAG
TVGCVGPRTPIAYMKYGCFCGLGGHGQPRDAIDWCCHGHDCCYTRAEEA
GCSPKTERYSWQCVNQSVLCGPAENKCQELLCKCDQEIANCLAQTEYNL
KYLFYPQFLCEPDSPKCD Human sPLA2-XIIA (UniProtKB/Swiss-Prot #Q9BZM1)
                                         (SEQ ID NO: 11)
MALLSRPALTLLLLLMAAVVRCQEQAQTTDWRATLKTIRNGVHKIDTYL
NAALDLLGGEDGLCQYKCSDGSKPFPRYGYKPSPPNGCGSPLFGVHLNI
GIPSLTKCCNQHDRCYETCGKSKNDCDEEFQYCLSKICRDVQKTLGLTQ
HVQACETTVELLFDSVIHLGCKPYLDSQRAACRCHYEEKTDL Human sPLA2-XIIB-like (UniProtKB/Swiss-Prot
Q9BX93)
                                         (SEQ ID NO: 12)
MKLASGFLVLWLSLGGGLAQSDTSPDTEESYSDWGLRHLRGSFESVNSY
FDSFLELLGGKNGVCQYRCRYGKAPMPRPGYKPQEPNGCGSYFLGLKVP
ESMDLGIPAMTKCCNQLDVCYDTCGANKYRCDAKFRWCLHSICSDLKRS
LGFVSKVEAACDSLVDTVFNTVWTLGCRPFMNSQRAACICAEEEKEEL
```

As would be appreciated by one of ordinary skill in the art, reagents that distinguish between various sPLA2 isoforms and allow one to detect isoform-specific expression are available and can be produced by known methods.

Evaluation of sPLA2 Expression and/or Activity

By analyzing a pattern of sPLA2 expression and/or activity in samples (e.g., samples of synovial fluid) obtained from subjects, such as healthy patients and from patients with OA, the present Applicants have found that it is possible to diagnose OA. In particular, elevated sPLA2-IIA expression without elevation of expression of other isoforms is indicative of OA. Thus, analysis of sPLA2 expression can be used to discriminate between normal/healthy and OA. In some embodiments, analysis of sPLA2 expression and/or activity patterns can be used to discriminate between early and late OA. In some embodiments, analysis of sPLA2 expression and/or activity patterns can be used to indicate risk for developing OA.

Accordingly, expression and/or activity of sPLA2-IIA (e.g., as compared to expression and/or activity of other sPLA2 isoforms) can be used to determine the subject's risk of developing OA, to diagnose OA, as well as to determine the degree of advancement of the disease (i.e., to determine the stage of the disease).

In certain embodiments, expression or activity of sPLA2-IIA is elevated if it is at least 2, 3, 4, 5, 6, 7, 8, 9, 10, 20, 50 or more times that of a level of expression or activity in a subject that does not have OA. In certain embodiments, expression or activity of one or more other sPLA2 isoforms (e.g., sPLA2-IB, sPLA2-IIC, sPLA2-IID, sPLA2-IIE, sPLA2-IIF, sPLA2-III, sPLA2-X, sPLA2-V, sPLA2-XIIA, or sPLA2-XIIB) is not elevated relative to a subject that does not have OA. The expression or activity level of other sPLA2 isoforms may be decreased or remain the same relative to a subject that does not have OA. The change in expression or activity of other sPLA2s between a subject that has OA and a subject that does not have OA may be below the detectable level (e.g., the level of change is not significant). As would be understood by one of skill in the art, determination of whether a sample exhibits elevated or lack of expression or activity can include comparison of expression or activity in the sample to a control. The control can be a sample from a subject that does not have OA (e.g., a healthy subject), or a reference value (e.g., a reference value obtained from analysis of a sample from a healthy subject), or a sample from a subject known to have OA.

It is contemplated that analysis of expression and/or activity levels of sPLA2 isoforms (e.g., sPLA2-IIA and at least one other isoform) can lead to the identification of sPLA2 expression and/or activity patterns. For example, a subject may have elevated levels of sPLA2-IIA while not having elevated levels of one or more other sPLA2 isoforms. The pattern of elevated sPLA2-IIA levels in the absence of elevated levels of other sPLA2s may be indicative of presence or risk for OA.

Diagnosis Methods

As will be appreciated by those of ordinary skill in the art, one or more biomarkers whose expression profiles correlate with OA (e.g., sPLA2-IIA, and additional biomarkers, such as additional sPLA2 isoforms), can diagnose OA, distinguish between different subtypes of OA and/or can discriminate between different stages of the disease may be used to identify, study or characterize unknown biological samples. Accordingly, the present invention provides methods for characterizing biological samples obtained from a subject suspected of having OA, for diagnosing OA in a subject, for identifying the subtype of OA, and for assessing the advancement of OA in a subject. In such methods, the biomarkers' activity or expression levels determined for a biological sample obtained from the subject are compared to the levels in one or more control samples. The control samples may be obtained from a healthy individual (or a group of healthy individuals), from an individual (or group of individuals) afflicted with OA, from an individual (or group of individuals) afflicted with subtype I OA or subtype II OA, and/or from an individual (or group of individuals) afflicted with a specific stage of the disease (e.g., early OA or late OA). As mentioned above, the control activity expression levels of the biomarkers of interest can be determined from a significant number of individuals, and an average or mean is obtained.

The present invention further provides methods for characterizing responsiveness to therapy, prognosis for disease course, and measurement of disease progression of OA in a subject. In such methods, the biomarkers' activity or expression levels determined for a biological sample obtained from the subject from one or more timepoints are compared to the levels from the subject from one or more other timepoints. For example, activity or expression levels of biomarkers may be measured before or at the beginning of a treatment course. Activity or expression levels may be measured at one or more timepoints throughout the course of treatment and compared with the level of activity or expression before the treatment. Selection of appropriate treatment can be guided using the information obtained in these methods.

All of the methods of evaluating OA described herein (e.g., to monitor therapy, progression, or abatement of disease), can also be applied to subjects having RA or suspected of having RA.

In some embodiments, methods herein are used to diagnose the presence or risk for OA in a subject suspected of having OA. Elevated sPLA2-IIA can be observed in rheumatoid arthritis (RA) patients as well as OA patients. The present invention encompasses the finding that other sPLA2 isoforms are often elevated in RA that are not elevated in OA (e.g., sPLA2-IIF, sPLA2-III, and sPLA2-V). Thus, the present invention provides methods of distinguishing OA from RA in a subject by determining a pattern of sPLA2 isoform expression and/or activity levels. For example, a subject may suffer from symptoms that are indicative of joint disease. One may determine the expression level and/or activity level of several sPLA2 isoforms in the subject. If, for example, the subject has elevated sPLA2-IIA, but also has elevated levels of one or more other sPLA2 isoforms, then one may determine that the subject does not have OA, and that the subject likely suffers from RA. Additionally, a practitioner can distinguish subjects suspected of having OA from subjects suspected of having RA on the bases such as the pattern of joint involvement and serological analyses for markers other than sPLA2. RA typically presents in distal joints in a symmetric pattern, whereas OA often presents in one or a few joints, without severe inflammation. Positivity in certain serological tests (e.g., for rhematoid factor, or in an anti-cyclic citrullinated peptide (anti-CCP) antibody test), for certain inflammatory markers (e.g., c-reactive protein, increased erythrocyte sedimentation rate (ESR)), and elevated cell counts (e.g., >1000/microliter) are often indicative of RA rather than OA.

Biological Samples

The methods of the invention may be applied to the study of any type of biological samples allowing one or more inventive biomarkers to be assayed. Examples of suitable biological samples include, but are not limited to, urine, blood, blood products, joint fluid, saliva, and synovial fluid. The biological samples used in the practice of the inventive methods of diagnostic may be fresh or frozen samples collected from a subject, or archival samples with known diagnosis, treatment and/or outcome history. Biological samples may be collected by any non-invasive means, such as, for example, by drawing blood from a subject, or using fine needle aspiration or needle biopsy. Alternatively, biological samples may be collected by an invasive method, including, for example, surgical biopsy.

In certain embodiments, the inventive methods are performed on the biological sample itself without or with limited processing of the sample.

In other embodiments, the inventive methods are performed at the single cell level (e.g., isolation of cells from the biological sample). However, in such embodiments, the inventive methods are preferably performed using a sample comprising many cells, where the assay is "averaging" expression over the entire collection of cells present in the sample. Preferably, there is enough of the biological sample to accurately and reliably determine the expression and/or activity of the set of biomarkers of interest. Multiple biological samples may be taken from the same tissue/body part in order to obtain a representative sampling of the tissue.

In still other embodiments, the inventive methods are performed on a protein extract prepared from the biological sample. Preferably, the protein extract contains the total protein content. However, the methods may also be performed on extracts containing one or more of: membrane proteins, nuclear proteins, and cytosolic proteins. Methods of protein extraction are well known in the art (see, for example "Protein Methods", D. M. Bollag et al., $2^{nd}$ Ed., 1996, Wiley-Liss; "*Protein Purification Methods: A Practical Approach*", E. L. Harris and S. Angal (Eds.), 1989; "*Protein Purification Techniques: A Practical Approach*", S. Roe, $2^{nd}$ Ed., 2001, Oxford University Press; "*Principles and Reactions of Protein Extraction, Purification, and Characterization*", H. Ahmed, 2005, CRC Press: Boca Raton, Fla.). Numerous different and versatile kits can be used to extract proteins from bodily fluids and tissues, and are commercially available from, for example, BioRad Laboratories (Hercules, Calif.), BD Biosciences Clontech (Mountain View, Calif.), Chemicon International, Inc. (Temecula, Calif.), Calbiochem (San Diego, Calif.), Pierce Biotechnology (Rockford, Ill.), and Invitrogen Corp. (Carlsbad, Calif.). User Guides that describe in great detail the protocol to be followed are usually included in all these kits. Sensitivity, processing time and costs may be different from one kit to another. One of ordinary skill in the art can easily select the kit(s) most appropriate for a particular situation. After the protein extract has been obtained, the protein concentration of the extract is preferably standardized to a value being the same as that of the control sample in order to allow signals of the protein markers to be quantitated. Such standardization can be made using photometric or spectrometric methods or gel electrophoresis.

In yet other embodiments, the inventive methods are performed on nucleic acid molecules extracted from the biological sample. For example, RNA may be extracted from the sample before analysis. Methods of RNA extraction are well known in the art (see, for example, J. Sambrook et al., "*Molecular Cloning: A Laboratory Manual*", 1989, $2^{nd}$ Ed., Cold Spring Harbor Laboratory Press: Cold Spring Harbor, N.Y.). Most methods of RNA isolation from bodily fluids or tissues are based on the disruption of the tissue in the presence of protein denaturants to quickly and effectively inactivate RNases. Isolated total RNA may then be further purified from the protein contaminants and concentrated by selective ethanol precipitations, phenol/chloroform extractions followed by isopropanol precipitation or cesium chloride, lithium chloride or cesium trifluoroacetate gradient centrifugations. Kits are also available to extract RNA (i.e., total RNA or mRNA) from bodily fluids or tissues and are commercially available from, for example, Ambion, Inc. (Austin, Tex.), Amersham Biosciences (Piscataway, N.J.), BD Biosciences Clontech (Palo Alto, Calif.), BioRad Laboratories (Hercules, Calif.), GIBCO BRL (Gaithersburg, Md.), and Qiagen, Inc. (Valencia, Calif.).

In certain embodiments, after extraction, mRNA is amplified, and transcribed into cDNA, which can then serve as template for multiple rounds of transcription by the appropriate RNA polymerase. Amplification methods are well known in the art (see, for example, A. R. Kimmel and S. L. Berger, Methods Enzymol. 1987, 152: 307-316; J. Sambrook et al., "*Molecular Cloning: A Laboratory Manual*", 1989, $2^{nd}$ Ed., Cold Spring Harbour Laboratory Press: New York; "*Short Protocols in Molecular Biology*", F. M. Ausubel (Ed.), 2002, $5^{th}$ Ed., John Wiley & Sons; U.S. Pat. Nos. 4,683,195; 4,683,202 and 4,800,159). Reverse transcription reactions may be carried out using non-specific primers, such as an anchored oligo-dT primer, or random sequence primers, or using a target-specific primer complementary to the RNA for each probe being monitored, or using thermostable DNA polymerases (such as avian myeloblastosis virus reverse transcriptase or Moloney murine leukemia virus reverse transcriptase).

Determination of Protein Expression Levels

The diagnostic methods of the present invention can involve the determination of expression of one polypeptide (e.g., sPLA2-IIA), or may involve the determination of expression levels of a plurality (i.e., one or more, e.g., at least 2, at least 3, at least 4, at least 5, at least 6, at least 7, at least 8, at least 9, at least 10 or more) of polypeptides in a biological sample obtained from a subject. Determination of protein expression levels in the practice of the inventive methods may be performed by any suitable method (see, for example, E. Harlow and A. Lane, "*Antibodies: A Laboratories Manual*", 1988, Cold Spring Harbor Laboratory: Cold Spring Harbor, N.Y.).

In general, protein expression levels are determined by contacting a biological sample isolated from a subject with binding agents for one or more of the protein markers; detecting, in the sample, the levels of polypeptides that bind to the binding agents; and comparing the levels of polypeptides in the sample with the levels of polypeptides in a control sample. As used herein, the term "binding agent" refers to an entity such as a polypeptide or antibody that specifically binds to an inventive protein marker. An entity "specifically binds" to a polypeptide if it reacts/interacts at a detectable level with the polypeptide but does not react/interact detectably with peptides containing unrelated sequences or sequences of different polypeptides.

In certain embodiments, the binding agent is a ribosome, with or without a peptide component, an RNA molecule, or a polypeptide (e.g., a polypeptide that comprises a polypeptide sequence of a protein marker, a peptide variant thereof, or a non-peptide mimetic of such a sequence).

In other embodiments, the binding agent is an antibody specific for a protein marker of the invention (e.g., an antibody specific for an sPLA2-IIA isoform). In some embodiments, the binding agent is an antibody that specifically binds to sPLA2-IIA, and which does not cross-react with other sPLA2 isoforms. Suitable antibodies for use in the methods of the present invention include monoclonal and polyclonal antibodies, immunologically active fragments (e.g., Fab or $(Fab)_2$ fragments), antibody heavy chains, humanized antibodies, antibody light chains, and chimeric antibodies. Antibodies, including monoclonal and polyclonal antibodies, fragments and chimeras, may be prepared using methods known in the art (see, for example, R. G. Mage and E. Lamoyi, in "*Monoclonal Antibody Production Techniques and Applications*", 1987, Marcel Dekker, Inc.: New York, pp. 79-97; G. Kohler and C. Milstein, Nature, 1975, 256: 495-497; D. Kozbor et al., J. Immunol. Methods, 1985, 81: 31-42; and R. J. Cote et al., Proc. Natl. Acad. Sci. 1983, 80: 2026-203; R. A. Lerner, Nature, 1982, 299: 593-596; A. C. Nairn et al., Nature, 1982, 299: 734-736; A. J. Czernik et al., Methods Enzymol. 1991, 201: 264-283; A. J. Czernik et al., Neurometbods: Regulatory Protein Modification: Techniques & Protocols, 1997, 30: 219-250; A. J. Czernik et al., Neuroprotocols, 1995, 6: 56-61; H. Zhang et al., J. Biol. Chem. 2002, 277: 39379-39387; S. L. Morrison et al., Proc. Natl. Acad. Sci., 1984, 81: 6851-6855; M. S, Neuberger et al., Nature, 1984, 312: 604-608; S. Takeda et al., Nature, 1985, 314: 452-454). Antibodies to be used in the methods of the invention can be purified by methods well known in the art (see, for example, S. A. Minden, "*Monoclonal Antibody Purification*", 1996, IBC Biomedical Library Series: Southbridge, Mass.). For example, antibodies can be affinity-purified by passage over a column to which a protein marker or fragment thereof is bound. The bound antibodies can then be eluted from the column using a buffer with a high salt concentration.

Instead of being prepared, antibodies to be used in the methods of the present invention may be obtained from scientific or commercial sources (e.g., Cayman Chemical).

In certain embodiments, the binding agent is directly or indirectly labeled with a detectable moiety. The role of a detectable agent is to facilitate the detection step of the diagnostic method by allowing visualization of the complex formed by binding of the binding agent to the protein marker (or analog or fragment thereof). Preferably, the detectable agent is selected such that it generates a signal which can be measured and whose intensity is related (preferably proportional) to the amount of protein marker present in the sample being analyzed. Methods for labeling biological molecules such as polypeptides and antibodies are well-known in the art (see, for example, "*Affinity Techniques. Enzyme Purification: Part B*", Methods in Enzymol., 1974, Vol. 34, W. B. Jakoby and M. Wilneck (Eds.), Academic Press: New York, N.Y.; and M. Wilchek and E. A. Bayer, Anal. Biochem., 1988, 171: 1-32).

Any of a wide variety of detectable agents can be used in the practice of the present invention. Suitable detectable agents include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

In certain embodiments, the binding agents (e.g., antibodies) may be immobilized on a carrier or support (e.g., a bead, a magnetic particle, a latex particle, a microtiter plate well, a cuvette, or other reaction vessel). Examples of suitable carrier or support materials include agarose, cellulose, nitrocellulose, dextran, Sephadex, Sepharose, liposomes, carboxymethyl cellulose, polyacrylamides, polystyrene, gabbros, filter paper, magnetite, ion-exchange resin, plastic film, plastic tube, glass, polyamine-methyl vinyl-ether-maleic acid copolymer, amino acid copolymer, ethylene-maleic acid copolymer, nylon, silk, and the like. Binding agents may be indirectly immobilized using second binding agents specific for the first binding agents (e.g., mouse antibodies specific for the protein markers may be immobilized using sheep anti-mouse IgG Fc fragment specific antibody coated on the carrier or support).

Protein expression levels in the diagnostic methods of the present invention may be determined using immunoassays. Examples of such assays are time resolved fluorescence immunoassays (TR-FIA), radioimmunoassays, enzyme immunoassays (e.g., ELISA), immunofluorescence immunoprecipitation, latex agglutination, hemagglutination, and histochemical tests, which are conventional methods well-known in the art. As will be appreciated by one skilled in the art, the immunoassay may be competitive or non-competitive. Methods of detection and quantification of the signal generated by the complex formed by binding of the binding agent with the protein marker will depend on the nature of the assay and of the detectable moiety (e.g., fluorescent moiety).

In certain embodiments, protein levels of sPLA2 isoforms may be determined using time resolved fluorescence immunoassays (TR-FIA). Anti-sPLA2 antibodies useful for TR-FIA have been generated previously in rabbits (Nevalainen et al., Biochem. Biophys. Acta. 1733:210-223, 2005). In some embodiments, TR-FIA includes the following steps: (1) isolation (e.g., on a Protein A column) of rabbit anti-sPLA2 IgG to generate "catching antibody"; (2) labeling (e.g., with Delfia Eu-labeling reagent) of rabbit anti-sPLA2 IgG to generate "detecting antibody"; (3) coating of assay wells (e.g., 96-well microtitration plates) with "catching antibody"; (4) addition of test sample (e.g., serum or synovial fluid) or standard solution to assay wells; (5) addition of "detecting antibody" to assay wells; (6) measurement of fluorescence at various emission wavelengths (e.g., 340 nm or 615 nm). In some embodiments, high levels of background fluorescence are reduced by preincubation of test sample (e.g., serum or synovial fluid) with IgG purified from non-immunized rabbit serum (e.g., "preimmune serum") for a given length of time (e.g., 60 minutes).

Alternatively, the protein expression levels may be determined using mass spectrometry based methods or image (including use of labeled ligand) based methods known in the art for the detection of proteins. Other suitable methods include proteomics-based methods. Proteomics, which studies the global changes of protein expression in a sample, can include the following steps: (1) separation of individual proteins in a sample by electrophoresis (1-D PAGE), (2) identification of individual proteins recovered from the gel (e.g., by mass spectrometry or N-terminal sequencing), and (3) analysis of the data using bioinformatics.

Determination of Polynucleotide Expression Levels

As already mentioned above, the diagnostic methods of the present invention may involve determination of the expression levels of nucleic acid molecules comprising polynucleotide sequences coding for one or more biomarkers (e.g., sPLA2-IIA). Determination of expression levels of nucleic acid molecules in the practice of the inventive methods may be performed by any suitable method, including, but not limited to, Southern analysis, Northern analysis, polymerase chain reaction (PCR) (see, for example, U.S. Pat. Nos., 4,683, 195; 4,683,202, and 6,040,166; "PCR Protocols: A Guide to Methods and Applications", Innis et al. (Eds.), 1990, Academic Press: New York), reverse transcriptase PCR(RT-PCT), anchored PCR, competitive PCR (see, for example, U.S. Pat. No. 5,747,251), rapid amplification of cDNA ends (RACE) (see, for example, "Gene Cloning and Analysis: Current Innovations, 1997, pp. 99-115); ligase chain reaction (LCR) (see, for example, EP 01 320 308), one-sided PCR (Ohara et al., Proc. Natl. Acad. Sci., 1989, 86: 5673-5677), in situ hybridization, Taqman-based assays (Holland et al., Proc. Natl. Acad. Sci., 1991, 88: 7276-7280), differential display (see, for example, Liang et al., Nucl. Acid. Res., 1993, 21: 3269-3275) and other RNA fingerprinting techniques, nucleic acid sequence based amplification (NASBA) and other transcription based amplification systems (see, for example, U.S. Pat. Nos. 5,409,818 and 5,554,527), Qbeta Replicase, Strand Displacement Amplification (SDA), Repair Chain Reaction (RCR), nuclease protection assays, subtraction-based methods, Rapid-Scan™, and the like.

Nucleic acid probes for use in the detection of polynucleotide sequences in biological samples may be constructed using conventional methods known in the art. Suitable probes may be based on nucleic acid sequences encoding at least 5 sequential amino acids from regions of nucleic acids encoding a protein marker, and preferably comprise about 15 to about 50 nucleotides. A nucleic acid probe may be labeled with a detectable moiety, as mentioned above in the case of binding agents. The association between the nucleic acid probe and detectable moiety can be covalent or non-covalent. Detectable moieties can be attached directly to nucleic acid probes or indirectly through a linker (E. S. Mansfield et al., Mol. Cell. Probes, 1995, 9: 145-156). Methods for labeling nucleic acid molecules are well-known in the art (for a review of labeling protocols, label detection techniques and recent developments in the field, see, for example, L. J. Kricka, Ann. Clin. Biochem. 2002, 39: 114-129; R. P. van Gijlswijk et al., Expert Rev. Mol. Diagn. 2001, 1: 81-91; and S. Joos et al., J. Biotechnol. 1994, 35: 135-153).

Nucleic acid probes may be used in hybridization techniques to detect polynucleotides encoding the protein markers. The technique generally involves contacting and incubating nucleic acid molecules in a biological sample obtained from a subject with the nucleic acid probes under conditions such that specific hybridization takes place between the nucleic acid probes and the complementary sequences in the nucleic acid molecules. After incubation, the non-hybridized nucleic acids are removed, and the presence and amount of nucleic acids that have hybridized to the probes are detected and quantified.

Detection of nucleic acid molecules comprising polynucleotide sequences coding for a protein marker may involve amplification of specific polynucleotide sequences using an amplification method such as PCR, followed by analysis of the amplified molecules using techniques known in the art. Suitable primers can be routinely designed by one skilled in the art. In order to maximize hybridization under assay conditions, primers and probes employed in the methods of the invention generally have at least 60%, preferably at least 75% and more preferably at least 90% identity to a portion of nucleic acids encoding a protein marker.

Hybridization and amplification techniques described herein may be used to assay qualitative and quantitative aspects of expression of nucleic acid molecules comprising polynucleotide sequences coding for the inventive protein markers.

Alternatively, oligonucleotides or longer fragments derived from nucleic acids encoding each protein marker may be used as targets in a microarray. A number of different array configurations and methods of their production are known to those skilled in the art (see, for example, U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637). Microarray technology allows for the measurement of the steady-state level of large numbers of polynucleotide sequences simultaneously. Microarrays currently in wide use include cDNA arrays and oligonucleotide arrays. Analyses using microarrays are generally based on measurements of the intensity of the signal received from a labeled probe used to detect a cDNA sequence from the sample that hybridizes to a nucleic acid probe immobilized at a known location on the microarray (see, for example, U.S. Pat. Nos. 6,004,755; 6,218,114; 6,218,122; and 6,271,002). Array-based gene expression methods are known in the art and have been described in numerous scientific publications as well as in patents (see, for example, M. Schena et al., Science, 1995, 270: 467-470; M. Schena et al., Proc. Natl. Acad. Sci. USA 1996, 93: 10614-10619; J. J. Chen et al., Genomics, 1998, 51: 313-324; U.S. Pat. Nos. 5,143,854; 5,445,934; 5,807,522; 5,837,832; 6,040,138; 6,045,996; 6,284,460; and 6,607,885).

Once the expression levels of a biomarker or biomarkers of interest (e.g., sPLA2-IIA) have been determined (as described above) for the biological sample being analyzed, they can be compared to the expression levels in one or more control samples. Comparison of expression levels according to methods of the present invention is preferably performed after the expression levels obtained have been corrected for both differences in the amount of sample assayed and variability in the quality of the sample used (e.g., amount of protein extracted, or amount and quality of mRNA tested). Correction may be carried out using different methods well-known in the art. For example, the protein concentration of a sample may be standardized using photometric or spectrometric methods or gel electrophoresis (as already mentioned above) before the sample is analyzed. In case of samples containing nucleic acid molecules, correction may be carried out by normalizing the levels against reference genes (e.g., housekeeping genes) in the same sample. Alternatively or additionally, normalization can be based on the mean or median signal (e.g., Ct in the case of RT-PCR) of all assayed genes or a large subset thereof (global normalization approach).

Determination of Activity Levels

The diagnostic methods of the present invention may involve determination of the activity levels of one or more biomarkers (e.g., sPLA2-IIA). Determination of activity levels of various sPLA2 enzymes in the practice of the inventive methods may be performed by any suitable method, including, but not limited to, spectrophotometric, fluorometric, chemiluminescent, radiometric, and calorimetric assays. Enzyme assays may include the use of any suitable substrate for the particular enzyme that is being tested. The methods can include use of isoform-specific substrates or inhibitors. For example, a fluorometric assay using a suitable substrate may be used to determine enzyme activity of certain sPLA2s (e.g., sPLA2-IIA, sPLA2-V, etc.) (see, for example, B. Smart, et al. Inhibition of the complete set of mammalian secreted phospholipases A2 by indole analogues: a structure-guided study; Bioorganic and Medicinal Chemistry, 2004, 12:1737-1749). In some embodiments, the substrate used is a pyrene-labeled phosphatidylglycerol.

Enzyme activity assays can be performed in any suitable plate, including, for example, an 8-well, 24-well, or 96-well microtiter plate. Fluorescence can be read by detection methods known in the art. For example, fluorescence levels can be measured by a microtiter plate spectrophotometer. Fluorescence levels of test samples (e.g., synovial fluid from a patient at risk for or having OA) can be compared to fluorescence levels in a reference sample to determine relative fluorescence, which can then be correlated to enzymatic activity Selection of Appropriate Treatment Using methods described herein, skilled physicians may select and prescribe treatments adapted to each individual patient based on the diagnosis and disease staging provided to the patient through determination of the expression and/or activity levels of sPLA2-IIA (and other biomarkers). In particular, the present invention provides physicians with a non-subjective means to diagnose early OA, which will allow for early treatment, when intervention is likely to have its greatest effect, potentially preventing pain and long-term disability and improving patient's quality of life. Selection of an appropriate therapeutic regimen for a given patient may be made based solely on the diagnosis/staging provided by the inventive methods. Alternatively, the physician may also consider other clinical or pathological parameters used in existing methods to diagnose OA and assess its advancement.

Furthermore, the methods of OA diagnosis, OA subtype identification, and OA staging provided by the present invention allow the disease to be monitored even when signs of cartilage destruction would not be visible or when changes in joint spaces would not be detectable on X-ray images.

Kits

In another aspect, the present invention provides kits comprising materials useful for carrying out diagnostic methods according to the present invention. The diagnosis/characterization/staging procedures described herein may be performed by diagnostic laboratories, experimental laboratories, or practitioners. The invention provides kits which can be used in these different settings.

Materials and reagents for characterizing biological samples, diagnosing OA in a subject, identifying OA subtype, and/or staging OA in a subject according to the inventive methods may be assembled together in a kit. In certain embodiments, an inventive kit comprises at least one reagent that specifically detects expression and/or activity levels of one or more biomarkers (e.g., sPLA2-IIA), and instructions for using the kit according to a method of the invention. Each kit may preferably comprise the reagent which renders the procedure specific. Thus, for detecting/quantifying a protein marker (or an analog or fragment thereof), the reagent that specifically detects expression levels of the protein may be an antibody that specifically binds to the protein marker (or analog or fragment thereof). For detecting/quantifying a nucleic acid molecule comprising a polynucleotide sequence coding a protein marker, the reagent that specifically detects expression levels may be a nucleic acid probe complementary to the polynucleotide sequence (e.g., cDNA or an oligonucleotide). The nucleic acid probe may or may not be immobilized on a substrate surface (e.g., beads, a microarray, and the like). For detecting/quantifying activity levels, the reagent that specifically detects activity levels may be a substrate that is specifically recognized by one or more biomarkers (e.g., sPLA2-IIA). The substrate that is recognized may become fluorescent when cleaved by the biomarker (e.g., sPLA2-IIA).

Additionally, inventive kits may include a substrate that inhibits sPLA2 activity. Various sPLA2 inhibitors are known in the art (See, for example, Oslund, et al. Highly specific and broadly potent inhibitors of mammalian secreted phoshpolipases $A_2$; 2008, J. Med. Chem.; 51(15):4708-14). Many sPLA2 inhibitors can function to inhibit the activity of more than one sPLA2 isoform. For example, compound 12a (from Oslund, et al. Highly specific and broadly potent inhibitors of mammalian secreted phoshpolipases $A_2$; 2008, J. Med. Chem.; 51(15):4708-14) inhibits the activity of several sPLA2 isoforms, including but not limited to sPLA2-IIA, sPLA2-V, and sPLA2-IIE. An additional example of a compound that inhibits the activity of several sPLA2 isoforms is compound R0050907A, the structure of which is shown below:

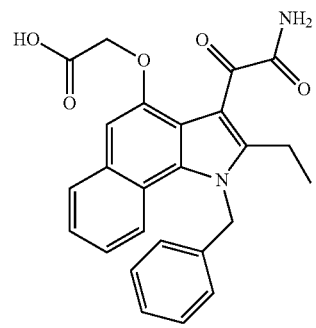

RO050907A (pan inh.)

However, several sPLA2 inhibitors have been found to preferentially inhibit one isoform of sPLA2. For example, compound 16b (from Oslund, et al. Highly specific and broadly potent inhibitors of mammalian secreted phoshpolipases $A_2$; 2008, J. Med. Chem.; 51(15):4708-14) inhibits the activity of sPLA2-IIA, while the activities of the other isoforms remain relatively unchanged. The present invention encompasses the finding that additional compounds may function as sPLA2 inhibitors that preferentially inhibit the activity of one or more isoforms of sPLA2 (e.g., sPLA2-IIA). For example, RO032107A and "Compound B" preferentially inhibit sPLA2-IIA. The structures of these compounds are as follows:

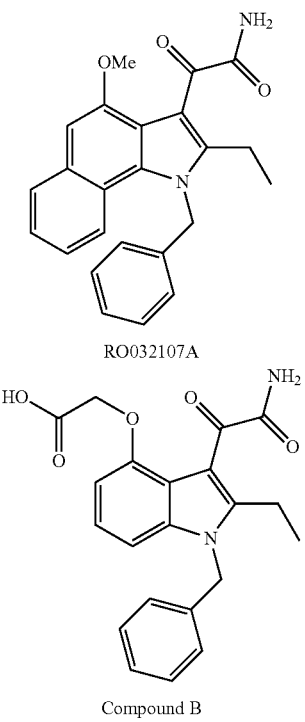

RO032107A

Compound B

In some embodiments, the inventive kits comprise a specific substrate that inhibits sPLA2-IIA activity. In some embodiments, the inventive kits comprise a specific substrate that inhibits activity of another sPLA2 isoform. In some embodiments, the inventive kits comprise a substrate the inhibits the activity of one or more sPLA2 isoforms.

Depending on the procedure, the kit may further comprise one or more of: extraction buffer and/or reagents, amplification buffer and/or reagents, hybridization buffer and/or reagents, immunodetection buffer and/or reagents, labeling buffer and/or reagents, and detection means. Protocols for using these buffers and reagents for performing different steps of the procedure may be included in the kit.

The reagents may be supplied in a solid (e.g., lyophilized) or liquid form. The kits of the present invention may optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps of the disclosed methods may also be provided. The individual containers of the kit are preferably maintained in close confinement for commercial sale.

In certain embodiments, the kits of the present invention further comprise control samples. In some embodiments, the inventive kits comprise at least one expression profile map for OA, OA subtype, and/or OA progression as described herein for use as comparison template. Preferably, the expression profile map is digital information stored in a computer-readable medium.

Instructions for using the kit according to one or more methods of the invention may comprise instructions for processing the biological sample obtained from the subject and/ or for performing the test, instructions for interpreting the results as well as a notice in the form prescribed by a governmental agency (e.g., FDA) regulating the manufacture, use or sale of pharmaceuticals or biological products.

EXAMPLES

The following examples describe some of the preferred modes of making and practicing the present invention. However, it should be understood that these examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Example 1

Detection of sPLA2 in Synovial Fluids

Human Synovial Fluid Analysis

Human synovial fluids from normal, OA and RA patients were obtained. Time-resolved fluorescence immunoassays of sPLA2s were performed using 5 µA of synovial fluid for analysis of sPLA2-IIA and 50 µl of synovial fluid for analysis of all other sPLA2 isoforms. Assays were performed in duplicate. Assay buffer (50 mM Tris, pH 7.8, 0.9% NaCl, 0.02% Tween-20, 0.05% $NaN_3$, filtered through a 0.45 micron membrane) was added to each well to bring the total volume to 100 ul. Samples were submitted to time-resolved fluorescence immunoassay as described previously (Nevalainen, et al. Biochim. Biophys. Acta. 2005, 1733: 210-223). For assay calibration, various amounts of each recombinant human sPLA2 (prepared as described in Singer, et al. J. Biol. Chem. 2002, 277: 48535-48549) were added to assay buffer to generate a standard curve. Blanks were run that contained 100 ul assay buffer alone.

Results

Figure 2:
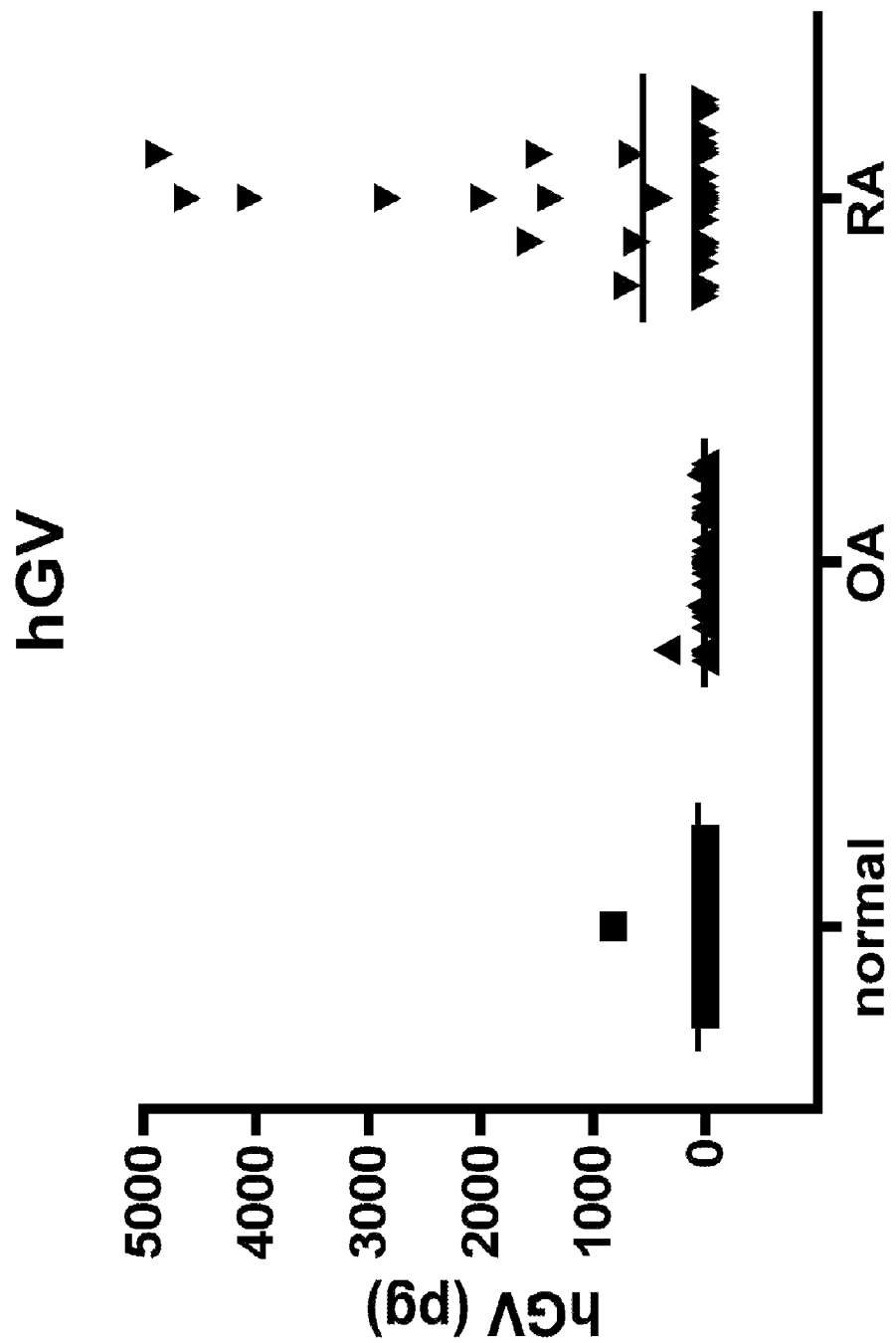
FIG. 2: Exemplary data demonstrating the quantitation by time resolved fluorescent immunoassay of human sPLA2-V levels in normal, OA, and RA human patients.
Figure 3:
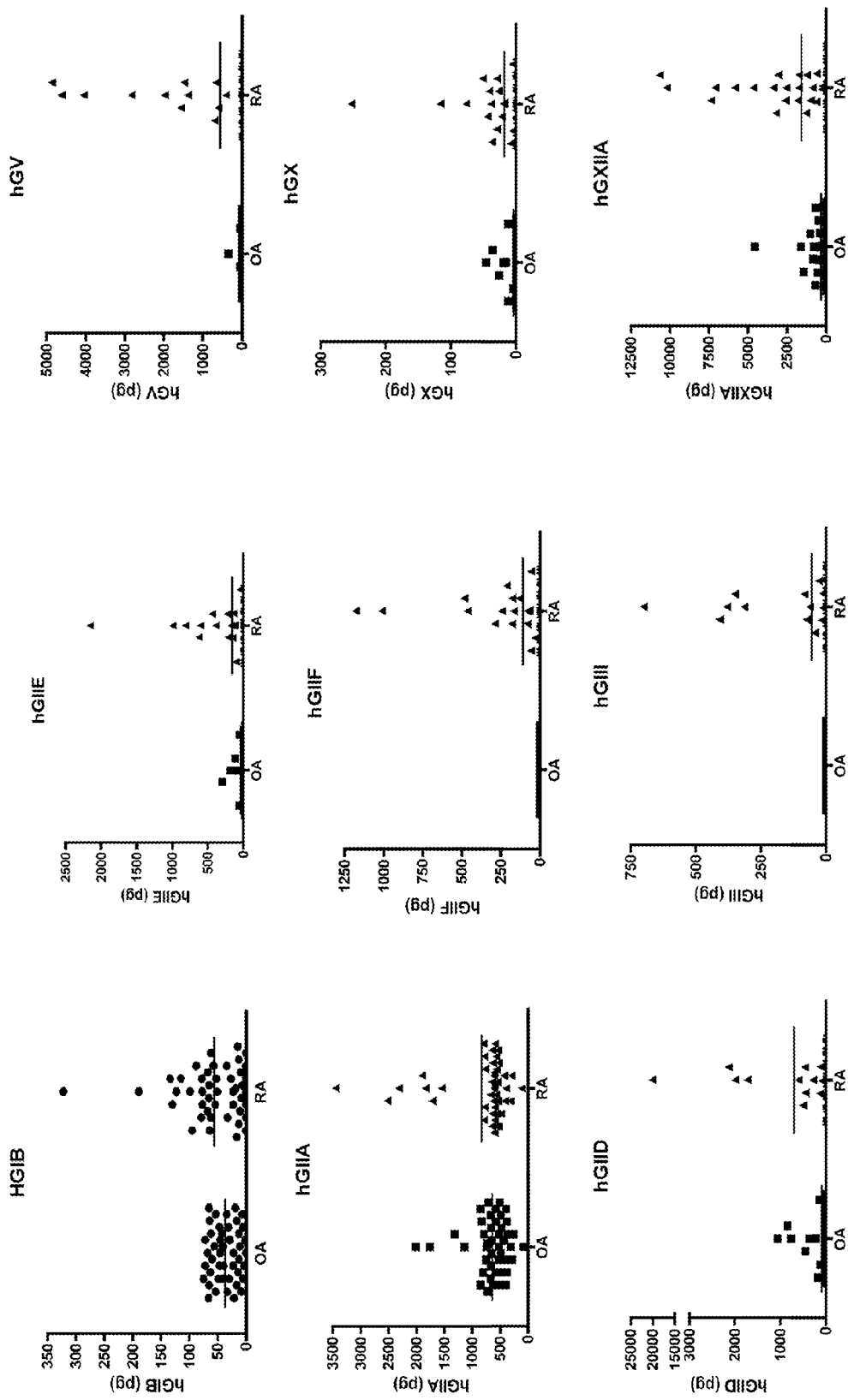
FIG. 3: Exemplary data demonstrating the quantitation by time resolved fluorescent immunoassay of human sPLA2-IB, -IIE, -III, -IIA, -IIF, -X, -IID, -V, and -XIIA isoform levels in OA and RA human patients.

Levels of sPLA2-IIA (FIG. 1) and sPLA2-V isoforms (FIG. 2) in synovial fluid from healthy volunteers, OA, and RA patients were quantified by time-resolved fluorescence immunoassays. Expression of sPLA2-IIA was elevated in OA and RA patients as compared to healthy patients. sPLA2-V was elevated in a number of RA patients. However, elevated sPLA2-V was detectable in synovial fluid from only one of the healthy volunteers and only one OA patient. FIG. 3 shows a quantitation of multiple sPLA2 isoforms in synovial fluid from 45 OA and 41 RA patients. Group IIA sPLA2 levels were by far the most highly expressed in these samples. These data show that expression of a particular isoform, sPLA2-IIA, and lack of elevated expression of other isoforms, is indicative of OA.

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A method of determining prognosis, presence of, risk for, progression or abatement of osteoarthritis in a subject, the method comprising:
   providing a biological sample from a subject;
   evaluating expression or activity of a first isoform of secretory phospholipase A2 (sPLA2) in the biological sample from the subject, wherein the first isoform is sPLA2 Group IIA (sPLA2-IIA);
   evaluating expression or activity of at least one other isoform of sPLA2 in the biological sample, and
   correlating expression or activity of sPLA2-IIA and the at least one other isoform of sPLA2 with a presence, risk, prognosis, progression, or abatement of arthritis.

2. The method of claim 1, wherein the at least one other isoform comprises one or more of sPLA2-IB, sPLA2-IIC, sPLA2-IID, sPLA2-IIE, sPLA2-IIF, sPLA2-III, sPLA2-X, sPLA2-V, sPLA2-XIIA, or sPLA2-XIIB.

3. The method of claim 1, wherein expression or activity of one or both of the first isoform of sPLA2 and at least one other isoform of sPLA2 are evaluated relative to one or more controls.

4. The method of claim 1, wherein expression or activity of one or both of the first isoform of sPLA2 and at least one other isoform of sPLA2 are evaluated at a first timepoint relative to one or more later timepoints.

5. The method of claim 1, wherein elevated expression or activity of sPLA2-IIA, and a lack of elevated expression or activity of the at least one other isoform of sPLA2, relative to expression or activity of sPLA2-IIA and the at least one other isoform of sPLA2 in a subject that does not have osteoarthritis, is correlated with the presence of, progression of, poor prognosis for, or risk for, osteoarthritis.

6. The method of claim 1, wherein the biological sample comprises synovial fluid, blood, a blood product, urine, or saliva from the subject.

7. The method of claim 6, wherein the biological sample comprises synovial fluid.

8. The method of claim 1, wherein expression of sPLA2-IIA polypeptides is evaluated.

9. The method of claim 8, wherein expression of sPLA2-IIA polypeptides is evaluated using an immunoassay.

10. The method of claim 1, wherein expression of polypeptides of the at least one other sPLA2 isoform is evaluated.

11. The method of claim 10, wherein expression of the at least one other sPLA2 isoform polypeptides is evaluated using an immunoassay.

12. The method of claim 1, wherein expression or activity of at least two of the other sPLA2 isoforms is evaluated.

13. The method of claim 1, wherein expression or activity of at least three of the other sPLA2 isoforms is evaluated.

14. The method of claim 1, wherein expression or activity of at least four of the other sPLA2 isoforms is evaluated.

15. The method of claim 12, wherein expression or activity of at least two of the following sPLA2 isoforms is evaluated: sPLA2-IIF, sPLA2-III, and sPLA2-V.

16. The method of claim 15, wherein expression or activity of sPLA2-IIF, sPLA2-III, and sPLA2-V is evaluated.

17. The method of claim 3, wherein the one or more controls comprises a sample from a subject that has been diagnosed with arthritis.

18. The method of claim 3, wherein the one or more controls comprises a sample from a subject that has been diagnosed with osteoarthritis.

19. The method of claim 1, wherein the subject is a human.

20. The method of claim 1, wherein the subject is a subject suffering from joint pain.

21. The method of claim 1, wherein the subject is suspected of having arthritis.

22. The method of claim 21, wherein the subject is suspected of having osteoarthritis.

23. The method of claim 1, wherein the subject is receiving therapy for arthritis.

24. A method of evaluating progression or abatement of osteoarthritis in a subject, the method comprising:
   providing a biological sample from a subject;
   evaluating expression or activity of a first isoform of secretory phospholipase A2 (sPLA2) in the biological sample, wherein the first isoform is sPLA2-IIA;
   evaluating expression or activity of at least one other isoform of sPLA2 in the biological sample, and
   correlating expression or activity of sPLA2-IIA and at least one other isoform of sPLA2 with progression or abatement of osteoarthritis in the subject.

25. The method of claim 24, wherein elevation of expression or activity of sPLA2-IIA and a lack of elevation of expression or activity of the at least one other isoform of sPLA2 in the subject over time is correlated with progression of osteoarthritis.

26. The method of claim 24, wherein the subject is receiving therapy for osteoarthritis, and wherein the subject's response to therapy is evaluated.

* * * * *

SEQUENCE LISTING

<160> NUMBER OF SEQ ID NOS: 12

<210> SEQ ID NO 1
<211> LENGTH: 997
<212> TYPE: DNA
<213> ORGANISM: Homo sapiens

<400> SEQUENCE: 1

```
gaaggaaaaa gagcaacaga tccagggagc attcacctgc cctgtctcca acagccttg      60
tgcctcacct accccaacc tcccagaggg agcagctatt taaggggagc aggagtgcag     120
aacaaacaag acggcctggg gatacaactc tggagtcctc tgagagagcc accaaggagg    180
agcaggggag cgacggccgg ggcagaagtt gagaccaccc agcagaggag ctaggccagt    240
ccatctgcat ttgtcaccca agaactctta ccatgaagac cctcctactg ttggcagtga    300
tcatgatctt tggcctactg caggcccatg ggaatttggt gaatttccac agaatgatca    360
agttgacgac aggaaaggaa gccgcactca gttatggctt ctacggctgc cactgtggcg    420
tgggtggcag aggatccccc aaggatgcaa cggatcgctg ctgtgtcact catgactgtt    480
gctacaaacg tctggagaaa cgtggatgtg gcaccaaatt tctgagctac aagtttagca    540
actcggggag cagaatcacc tgtgcaaaac aggactcctg cagaagtcaa ctgtgtgagt    600
gtgataaggc tgctgccacc tgttttgcta gaaacaagac gacctacaat aaaaagtacc    660
agtactattc caataaacac tgcagaggga gcacccctcg ttgctgagtc ccctcttccc    720
tggaaacctt ccacccagtg ctgaatttcc ctctctcata ccctccctcc ctaccctaac    780
caagttcctt ggccatgcag aaagcatccc tcacccatcc tagaggccag gcaggagccc    840
ttctataccc acccagaatg agacatccag cagatttcca gccttctact gctctcctcc    900
acctcaactc cgtgcttaac caaagaagct gtactccggg gggtctcttc tgaataaagc    960
aattagcaaa aaaaaaaaa aaaaaaaaa aaaaaaa                              997
```

<210> SEQ ID NO 2
<211> LENGTH: 144
<212> TYPE: PRT
<213> ORGANISM: Homo sapiens

<400> SEQUENCE: 2

```
Met Lys Thr Leu Leu Leu Ala Val Ile Met Ile Phe Gly Leu Leu
1               5                   10                  15

Gln Ala His Gly Asn Leu Val Asn Phe His Arg Met Ile Lys Leu Thr
            20                  25                  30

Thr Gly Lys Glu Ala Ala Leu Ser Tyr Gly Phe Tyr Gly Cys His Cys
        35                  40                  45

Gly Val Gly Gly Arg Gly Ser Pro Lys Asp Ala Thr Asp Arg Cys Cys
    50                  55                  60

Val Thr His Asp Cys Cys Tyr Lys Arg Leu Glu Lys Arg Gly Cys Gly
65                  70                  75                  80

Thr Lys Phe Leu Ser Tyr Lys Phe Ser Asn Ser Gly Ser Arg Ile Thr
                85                  90                  95

Cys Ala Lys Gln Asp Ser Cys Arg Ser Gln Leu Cys Glu Cys Asp Lys
            100                 105                 110

Ala Ala Ala Thr Cys Phe Ala Arg Asn Lys Thr Thr Tyr Asn Lys Lys
        115                 120                 125

Tyr Gln Tyr Tyr Ser Asn Lys His Cys Arg Gly Ser Thr Pro Arg Cys
    130                 135                 140
```

<210> SEQ ID NO 3
<211> LENGTH: 1911
<212> TYPE: DNA
<213> ORGANISM: Homo sapiens

<400> SEQUENCE: 3

```
cagggttcta cccggctggg tccaggcaga agttttcct ccccacctcc gggtttgtcc        60
tcatcatcgg tcactcccat tcacagcttt aagattctgg aggccaagaa tttgactccc       120
cccgatcca tggtctgtgg ataccaatgt tccgactgga cacggggagc ccgcgagacc        180
cgggtctcca gggtctgccc aaggaagttg ctcatgggag cagacctcta gagcaggatt       240
tgaggccagg ccaaagagaa ccccagagat gaaaggcctc ctcccactgg cttggttcct       300
ggcttgtagt gtgcctgctg tgcaaggagg cttgctggac ctaaaatcaa tgatcgagaa       360
ggtgacaggg aagaacgccc tgacaaacta cggcttctac ggctgttact gcggctgggg       420
cggccgagga accccaagg atggcaccga ttggtgctgt tgggcgcatg accactgcta        480
tgggcggctg gaggagaagg gctgcaacat cgcacacag tcctacaaat acagattcgc        540
gtggggcgtg tcacctgcg agcccgggcc cttctgccat gtgaacctct gtgcctgtga        600
ccggaagctc gtctactgcc tcaagagaaa cctacggagc tacaacccac agtaccaata       660
ctttcccaac atcctctgct cctaggcctc cccagcgagc cctcccaga ccaagacttt        720
tgttctgttt ttctacaaca cagagtactg actctgcctg gttcctgaga gaggctccta      780
agtcacagac ctcagtcttt ctcgaagctt ggcggacccc cagggccaca ctgtaccctc      840
cagcgagtcc caggagagtg actctggtca taggacttgg tagggtccca gggtccctag      900
gcctccactt ctgagggcag cccctctggt gccaagagct ctcctccaac tcagggttgg      960
ctgtgtctct tttcttctct gaagacagcg tcctggctcc agttggaaca cttcctgag     1020
atgcacttac ttctcagctt ctgcgatcag attatcatca ccaccaccct ccagagaatt    1080
tttacgcaag aagagccaaa ttgactctct aaatctggtg tatgggtatt aaataaaatt    1140
cattctcaag gctaataaaa accacattgg cattttcctc tgctgtgggg gatcgctggt    1200
gcctctttct ctgccactgg ggcaataaac ccaaagatgt ctacattatc tccgaaacag    1260
aagggaagat tagtaaatgc agggttttct gggatgagct tcaggctttc tcttgggcta    1320
atttttcttac accttgggt cctctccagt attgggtctc attcttcctc gatgggtca     1380
gggaaagata actggtgatt atgccagctt cagcttccag gccagagagg gtggcattca    1440
aatcccagtg ctggcttctt cagctgtgtg gtcttggacc cgttactgaa cctctttgac    1500
tttcagtctc tttgagaaat aaactgtctt gttccttgca atgtaaaatg agacttctaa    1560
agcccacctt gatgctgata tggagaatgc tgaggttcta ggatttcaca cagcaggaat    1620
tttttttaa taggtgtcag ctgtggggtt tatttttac aaagtaagga cattaaaaaa       1680
accaacccgt ctatcaattc ataaaagaaa ggatgttctg ataccaagac tgaaagaaga    1740
aaggatgtat tccaaaacaa aggaacatcc ttccaagaaa ggacctatgg cttctttatt    1800
ccgacatacc ccaaaataac tgcatgataa ataggtctat atttaaaaag ctctagtgtc    1860
gaatgttttc aaaataaaat ttaatttat gagaaaaaaa aaaaaaaaa a              1911
```

<210> SEQ ID NO 4
<211> LENGTH: 138
<212> TYPE: PRT
<213> ORGANISM: Homo sapiens

<400> SEQUENCE: 4

```
Met Lys Gly Leu Leu Pro Leu Ala Trp Phe Leu Ala Cys Ser Val Pro
1               5                   10                  15

Ala Val Gln Gly Gly Leu Leu Asp Leu Lys Ser Met Ile Glu Lys Val
            20                  25                  30

Thr Gly Lys Asn Ala Leu Thr Asn Tyr Gly Phe Tyr Gly Cys Tyr Cys
        35                  40                  45

Gly Trp Gly Gly Arg Gly Thr Pro Lys Asp Gly Thr Asp Trp Cys Cys
    50                  55                  60

Trp Ala His Asp His Cys Tyr Gly Arg Leu Glu Glu Lys Gly Cys Asn
65                  70                  75                  80

Ile Arg Thr Gln Ser Tyr Lys Tyr Arg Phe Ala Trp Gly Val Val Thr
                85                  90                  95

Cys Glu Pro Gly Pro Phe Cys His Val Asn Leu Cys Ala Cys Asp Arg
            100                 105                 110

Lys Leu Val Tyr Cys Leu Lys Arg Asn Leu Arg Ser Tyr Asn Pro Gln
        115                 120                 125

Tyr Gln Tyr Phe Pro Asn Ile Leu Cys Ser
    130                 135
```

<210> SEQ ID NO 5
<211> LENGTH: 148
<212> TYPE: PRT
<213> ORGANISM: Homo sapiens

<400> SEQUENCE: 5

```
Met Lys Leu Leu Val Leu Ala Val Leu Leu Thr Val Ala Ala Ala Asp
1               5                   10                  15

Ser Gly Ile Ser Pro Arg Ala Val Trp Gln Phe Arg Lys Met Ile Lys
            20                  25                  30

Cys Val Ile Pro Gly Ser Asp Pro Phe Leu Glu Tyr Asn Asn Tyr Gly
        35                  40                  45

Cys Tyr Cys Gly Leu Gly Gly Ser Gly Thr Pro Val Asp Glu Leu Asp
    50                  55                  60

Lys Cys Cys Gln Thr His Asp Asn Cys Tyr Asp Gln Ala Lys Lys Leu
65                  70                  75                  80

Asp Ser Cys Lys Phe Leu Leu Asp Asn Pro Tyr Thr His Thr Tyr Ser
                85                  90                  95

Tyr Ser Cys Ser Gly Ser Ala Ile Thr Cys Ser Ser Lys Asn Lys Glu
            100                 105                 110

Cys Glu Ala Phe Ile Cys Asn Cys Asp Arg Asn Ala Ala Ile Cys Phe
        115                 120                 125

Ser Lys Ala Pro Tyr Asn Lys Ala His Lys Asn Leu Asp Thr Lys Lys
    130                 135                 140

Tyr Cys Gln Ser
145
```

<210> SEQ ID NO 6
<211> LENGTH: 145
<212> TYPE: PRT
<213> ORGANISM: Homo sapiens

<400> SEQUENCE: 6

```
Met Glu Leu Ala Leu Leu Cys Gly Leu Val Val Met Ala Gly Val Ile
1               5                   10                  15

Pro Ile Gln Gly Gly Ile Leu Asn Leu Asn Lys Met Val Lys Gln Val
            20                  25                  30
```

```
Thr Gly Lys Met Pro Ile Leu Ser Tyr Trp Pro Tyr Gly Cys His Cys
         35                  40                  45

Gly Leu Gly Gly Arg Gly Gln Pro Lys Asp Ala Thr Asp Trp Cys Cys
     50                  55                  60

Gln Thr His Asp Cys Cys Tyr Asp His Leu Lys Thr Gln Gly Cys Ser
 65                  70                  75                  80

Ile Tyr Lys Asp Tyr Tyr Arg Tyr Asn Phe Ser Gln Gly Asn Ile His
                 85                  90                  95

Cys Ser Asp Lys Gly Ser Trp Cys Glu Gln Gln Leu Cys Ala Cys Asp
                100                 105                 110

Lys Glu Val Ala Phe Cys Leu Lys Arg Asn Leu Asp Thr Tyr Gln Lys
            115                 120                 125

Arg Leu Arg Phe Tyr Trp Arg Pro His Cys Arg Gly Gln Thr Pro Gly
        130                 135                 140

Cys
145

<210> SEQ ID NO 7
<211> LENGTH: 142
<212> TYPE: PRT
<213> ORGANISM: Homo sapiens

<400> SEQUENCE: 7

Met Lys Ser Pro His Val Leu Val Phe Leu Cys Leu Leu Val Ala Leu
 1               5                  10                  15

Val Thr Gly Asn Leu Val Gln Phe Gly Val Met Ile Glu Lys Met Thr
            20                  25                  30

Gly Lys Ser Ala Leu Gln Tyr Asn Asp Tyr Gly Cys Tyr Cys Gly Ile
        35                  40                  45

Gly Gly Ser His Trp Pro Val Asp Gln Thr Asp Trp Cys Cys His Ala
     50                  55                  60

His Asp Cys Cys Tyr Gly Arg Leu Glu Lys Leu Gly Cys Glu Pro Lys
 65                  70                  75                  80

Leu Glu Lys Tyr Leu Phe Ser Val Ser Glu Arg Gly Ile Phe Cys Ala
                 85                  90                  95

Gly Arg Thr Thr Cys Gln Arg Leu Thr Cys Glu Cys Asp Lys Arg Ala
                100                 105                 110

Ala Leu Cys Phe Arg Arg Asn Leu Gly Thr Tyr Asn Arg Lys Tyr Ala
            115                 120                 125

His Tyr Pro Asn Lys Leu Cys Thr Gly Pro Thr Pro Pro Cys
        130                 135                 140

<210> SEQ ID NO 8
<211> LENGTH: 168
<212> TYPE: PRT
<213> ORGANISM: Homo sapiens

<400> SEQUENCE: 8

Met Lys Lys Phe Phe Thr Val Ala Ile Leu Ala Gly Ser Val Leu Ser
 1               5                  10                  15

Thr Ala His Gly Ser Leu Leu Asn Leu Lys Ala Met Val Glu Ala Val
            20                  25                  30

Thr Gly Arg Ser Ala Ile Leu Ser Phe Val Gly Tyr Gly Cys Tyr Cys
        35                  40                  45

Gly Leu Gly Gly Arg Gly Gln Pro Lys Asp Glu Val Asp Trp Cys Cys
     50                  55                  60
```

```
His Ala His Asp Cys Cys Tyr Gln Glu Leu Phe Asp Gln Gly Cys His
 65                  70                  75                  80

Pro Tyr Val Asp His Tyr Asp His Thr Ile Glu Asn Asn Thr Glu Ile
                 85                  90                  95

Val Cys Ser Asp Leu Asn Lys Thr Glu Cys Asp Lys Gln Thr Cys Met
            100                 105                 110

Cys Asp Lys Asn Met Val Leu Cys Leu Met Asn Gln Thr Tyr Arg Glu
        115                 120                 125

Glu Tyr Arg Gly Phe Leu Asn Val Tyr Cys Gln Gly Pro Thr Pro Asn
    130                 135                 140

Cys Ser Ile Tyr Glu Pro Pro Glu Glu Val Thr Cys Ser His Gln
145                 150                 155                 160

Ser Pro Ala Pro Pro Ala Pro Pro
                165

<210> SEQ ID NO 9
<211> LENGTH: 509
<212> TYPE: PRT
<213> ORGANISM: Homo sapiens

<400> SEQUENCE: 9

Met Gly Val Gln Ala Gly Leu Phe Gly Met Leu Gly Phe Leu Gly Val
  1               5                  10                  15

Ala Leu Gly Gly Ser Pro Ala Leu Arg Trp Tyr Arg Thr Ser Cys His
             20                  25                  30

Leu Thr Lys Ala Val Pro Gly Asn Pro Leu Gly Tyr Leu Ser Phe Leu
         35                  40                  45

Ala Lys Asp Ala Gln Gly Leu Ala Leu Ile His Ala Arg Trp Asp Ala
     50                  55                  60

His Arg Arg Leu Gln Ser Cys Ser Trp Glu Asp Pro Glu Leu Thr
 65                  70                  75                  80

Ala Ala Tyr Gly Ala Leu Cys Ala His Glu Thr Ala Trp Gly Ser Phe
             85                  90                  95

Ile His Thr Pro Gly Pro Glu Leu Gln Arg Ala Leu Ala Thr Leu Gln
            100                 105                 110

Ser Gln Trp Glu Ala Cys Arg Ala Leu Glu Glu Ser Pro Ala Gly Ala
        115                 120                 125

Arg Lys Lys Arg Ala Ala Gly Gln Ser Gly Val Pro Gly Gly Gly His
    130                 135                 140

Gln Arg Glu Lys Arg Gly Trp Thr Met Pro Gly Thr Leu Trp Cys Gly
145                 150                 155                 160

Val Gly Asp Ser Ala Gly Asn Ser Ser Glu Leu Gly Val Phe Gln Gly
                165                 170                 175

Pro Asp Leu Cys Cys Arg Glu His Asp Arg Cys Pro Gln Asn Ile Ser
            180                 185                 190

Pro Leu Gln Tyr Asn Tyr Gly Ile Arg Asn Tyr Arg Phe His Thr Ile
        195                 200                 205

Ser His Cys Asp Cys Asp Thr Arg Phe Gln Gln Cys Leu Gln Asn Gln
    210                 215                 220

His Asp Ser Ile Ser Asp Ile Val Gly Val Ala Phe Phe Asn Val Leu
225                 230                 235                 240

Glu Ile Pro Cys Phe Val Leu Glu Glu Gln Glu Ala Cys Val Ala Trp
                245                 250                 255

Tyr Trp Trp Gly Gly Cys Arg Met Tyr Gly Thr Val Pro Leu Ala Arg
            260                 265                 270
```

```
Leu Gln Pro Arg Thr Phe Tyr Asn Ala Ser Trp Ser Ser Arg Ala Thr
        275                 280                 285

Ser Pro Thr Pro Ser Ser Arg Ser Pro Ala Pro Pro Lys Pro Arg Gln
        290                 295                 300

Lys Gln His Leu Arg Lys Gly Pro Pro His Gln Lys Gly Ser Lys Arg
305                 310                 315                 320

Pro Ser Lys Ala Asn Thr Thr Ala Leu Gln Asp Pro Met Val Ser Pro
                325                 330                 335

Arg Leu Asp Val Ala Pro Thr Gly Leu Gln Gly Pro Gln Gly Gly Leu
                340                 345                 350

Lys Pro Gln Gly Ala Arg Trp Val Cys Arg Ser Phe Arg His Leu
                355                 360                 365

Asp Gln Cys Glu His Gln Ile Gly Pro Arg Glu Ile Glu Phe Gln Leu
        370                 375                 380

Leu Asn Ser Ala Gln Glu Pro Leu Phe His Cys Asn Cys Thr Arg Arg
385                 390                 395                 400

Leu Ala Arg Phe Leu Arg Leu His Ser Pro Pro Glu Val Thr Asn Met
                405                 410                 415

Leu Trp Glu Leu Leu Gly Thr Thr Cys Phe Lys Leu Ala Pro Pro Leu
        420                 425                 430

Asp Cys Val Glu Gly Lys Asn Cys Ser Arg Asp Pro Arg Ala Ile Arg
        435                 440                 445

Val Ser Ala Arg His Leu Arg Arg Leu Gln Arg Arg His Gln Leu
450                 455                 460

Gln Asp Lys Gly Thr Asp Glu Arg Gln Pro Trp Pro Ser Glu Pro Leu
465                 470                 475                 480

Arg Gly Pro Met Ser Phe Tyr Asn Gln Cys Leu Gln Leu Thr Gln Ala
                485                 490                 495

Ala Arg Arg Pro Asp Arg Gln Gln Lys Ser Trp Ser Gln
                500                 505

<210> SEQ ID NO 10
<211> LENGTH: 165
<212> TYPE: PRT
<213> ORGANISM: Homo sapiens

<400> SEQUENCE: 10

Met Gly Pro Leu Pro Val Cys Leu Pro Ile Met Leu Leu Leu Leu Leu
1               5                   10                  15

Pro Ser Leu Leu Leu Leu Leu Leu Pro Gly Pro Gly Ser Gly Glu
            20                  25                  30

Ala Ser Arg Ile Leu Arg Val His Arg Arg Gly Ile Leu Glu Leu Ala
            35                  40                  45

Gly Thr Val Gly Cys Val Gly Pro Arg Thr Pro Ile Ala Tyr Met Lys
        50                  55                  60

Tyr Gly Cys Phe Cys Gly Leu Gly Gly His Gly Gln Pro Arg Asp Ala
65                  70                  75                  80

Ile Asp Trp Cys Cys His Gly His Asp Cys Cys Tyr Thr Arg Ala Glu
                85                  90                  95

Glu Ala Gly Cys Ser Pro Lys Thr Glu Arg Tyr Ser Trp Gln Cys Val
            100                 105                 110

Asn Gln Ser Val Leu Cys Gly Pro Ala Glu Asn Lys Cys Gln Glu Leu
            115                 120                 125

Leu Cys Lys Cys Asp Gln Glu Ile Ala Asn Cys Leu Ala Gln Thr Glu
        130                 135                 140
```

```
Tyr Asn Leu Lys Tyr Leu Phe Tyr Pro Gln Phe Cys Glu Pro Asp
145                 150                 155                 160

Ser Pro Lys Cys Asp
                165
```

<210> SEQ ID NO 11
<211> LENGTH: 189
<212> TYPE: PRT
<213> ORGANISM: Homo sapiens

<400> SEQUENCE: 11

```
Met Ala Leu Leu Ser Arg Pro Ala Leu Thr Leu Leu Leu Leu Met
1               5                   10                  15

Ala Ala Val Val Arg Cys Gln Glu Gln Ala Gln Thr Thr Asp Trp Arg
                20                  25                  30

Ala Thr Leu Lys Thr Ile Arg Asn Gly Val His Lys Ile Asp Thr Tyr
            35                  40                  45

Leu Asn Ala Ala Leu Asp Leu Leu Gly Gly Asp Gly Leu Cys Gln
        50                  55                  60

Tyr Lys Cys Ser Asp Gly Ser Lys Pro Phe Pro Arg Tyr Gly Tyr Lys
65                  70                  75                  80

Pro Ser Pro Pro Asn Gly Cys Gly Ser Pro Leu Phe Gly Val His Leu
                85                  90                  95

Asn Ile Gly Ile Pro Ser Leu Thr Lys Cys Cys Asn Gln His Asp Arg
                100                 105                 110

Cys Tyr Glu Thr Cys Gly Lys Ser Lys Asn Asp Cys Asp Glu Glu Phe
                115                 120                 125

Gln Tyr Cys Leu Ser Lys Ile Cys Arg Asp Val Gln Lys Thr Leu Gly
        130                 135                 140

Leu Thr Gln His Val Gln Ala Cys Glu Thr Thr Val Glu Leu Leu Phe
145                 150                 155                 160

Asp Ser Val Ile His Leu Gly Cys Lys Pro Tyr Leu Asp Ser Gln Arg
                165                 170                 175

Ala Ala Cys Arg Cys His Tyr Glu Glu Lys Thr Asp Leu
                180                 185
```

<210> SEQ ID NO 12
<211> LENGTH: 195
<212> TYPE: PRT
<213> ORGANISM: Homo sapiens

<400> SEQUENCE: 12

```
Met Lys Leu Ala Ser Gly Phe Leu Val Leu Trp Leu Ser Leu Gly Gly
1               5                   10                  15

Gly Leu Ala Gln Ser Asp Thr Ser Pro Asp Thr Glu Gly Ser Tyr Ser
                20                  25                  30

Asp Trp Gly Leu Arg His Leu Arg Gly Ser Phe Glu Ser Val Asn Ser
            35                  40                  45

Tyr Phe Asp Ser Phe Leu Glu Leu Leu Gly Gly Lys Asn Gly Val Cys
        50                  55                  60

Gln Tyr Arg Cys Arg Tyr Gly Lys Ala Pro Met Pro Arg Pro Gly Tyr
65                  70                  75                  80

Lys Pro Gln Glu Pro Asn Gly Cys Gly Ser Tyr Phe Leu Gly Leu Lys
                85                  90                  95

Val Pro Glu Ser Met Asp Leu Gly Ile Pro Ala Met Thr Lys Cys Cys
                100                 105                 110
```

```
                    -continued

Asn Gln Leu Asp Val Cys Tyr Asp Thr Cys Gly Ala Asn Lys Tyr Arg
        115             120             125

Cys Asp Ala Lys Phe Arg Trp Cys Leu His Ser Ile Cys Ser Asp Leu
    130             135                 140

Lys Arg Ser Leu Gly Phe Val Ser Lys Val Glu Ala Ala Cys Asp Ser
145             150             155                     160

Leu Val Asp Thr Val Phe Asn Thr Val Trp Thr Leu Gly Cys Arg Pro
            165             170                     175

Phe Met Asn Ser Gln Arg Ala Ala Cys Ile Cys Ala Glu Glu Glu Lys
            180             185                 190

Glu Glu Leu
        195
```